(12) United States Patent
Chu et al.

(10) Patent No.: US 8,974,815 B2
(45) Date of Patent: Mar. 10, 2015

(54) FIBROUS MEMBRANE FOR BIOMEDICAL APPLICATION BASED ON POLY(ESTER-AMIDE)S

(75) Inventors: Chih-Chang Chu, Ithaca, NY (US); Lei Li, West Chester, OH (US); Patti Jo Lewis, Highland Park, NJ (US)

(73) Assignee: Cornell University, Ithaca, NY (US)

( * ) Notice: Subject to any disclaimer, the term of this patent is extended or adjusted under 35 U.S.C. 154(b) by 1086 days.

(21) Appl. No.: 12/370,122

(22) Filed: Feb. 12, 2009

(65) Prior Publication Data

US 2009/0232874 A1  Sep. 17, 2009

Related U.S. Application Data

(63) Continuation-in-part of application No. 11/633,665, filed on Dec. 5, 2006, now abandoned.

(60) Provisional application No. 60/750,834, filed on Dec. 16, 2005, provisional application No. 61/064,033, filed on Feb. 12, 2008.

(51) Int. Cl.
*A61F 13/00* (2006.01)
*A01N 59/16* (2006.01)

(52) U.S. Cl.
USPC .......................... 424/443; 424/650; 514/315

(58) Field of Classification Search
USPC ................................................ 424/443, 650
See application file for complete search history.

(56) References Cited

U.S. PATENT DOCUMENTS

| 5,516,881 A | 5/1996 | Lee et al. |
| 6,503,538 B1* | 1/2003 | Chu et al. ...................... 424/497 |
| 7,105,228 B2* | 9/2006 | Averdung et al. ............. 428/398 |
| 2004/0126405 A1* | 7/2004 | Sahatjian et al. ............. 424/423 |
| 2004/0170685 A1* | 9/2004 | Carpenter et al. ............ 424/468 |
| 2006/0024357 A1 | 2/2006 | Carpenter et al. |
| 2007/0155273 A1 | 7/2007 | Chu et al. |

FOREIGN PATENT DOCUMENTS

WO  WO 02/18477 A2  3/2002

OTHER PUBLICATIONS

Thandavamoorthy Subbiah et al., "Electrospinning of Nanofibers," Feb. 15, 2005, Journal of Applied Polymer Science, vol. 96 Issue 2, abstract and pp. 557-569.*
Katsarava, R., et al., "Amino Acid-Based Bioanalogous Polymers. Synthesis, and Study of Regular Poly(ester amlde)s Based on Bis(α-amino acid) α,ω-Alkylene Dlesters, and Aliphatic Dicarboxylic Acids", J. Poly. Sci.: Part A: Poly. Chem., vol. 37, 391-407 (1999).
Carraher, Jr., C.E., "Seymour/Carraher's Polymer Chemistry", Fifth Edition, Revised and Expanded, Marcel Dekker, Inc., New York—Basel, 2000, 270-271.
Lewis, Patti J., "A Novel Scaffold for Tissue Engineering", Thesis—Cornell University.

(Continued)

*Primary Examiner* — Lynda Salvatore
(74) *Attorney, Agent, or Firm* — Harris Beach PLLC

(57) ABSTRACT

Electrospun biodegradable poly(ester-amide) fabric is especially suitable as a scaffold for tissue engineering and to incorporate drug for burn or wound healing treatment to accelerate healing, or to prevent tissue adhesion after surgery.

11 Claims, 10 Drawing Sheets

(56) References Cited

OTHER PUBLICATIONS

International Searching Authority, Notification of Transmittal of the International Search Report and the Written Opinion of the International Searching Authority, or the Declaration, International Search Report for PCT/US09/00885 mailed Apr. 2, 2009 (3 pgs.).

International Search Report and Written Opinion of the International Searching Authority for International Patent Application No. PCT/US09/00885 mailed Apr. 2, 2009 (8 pgs.).

Carraher, Jr., C.E., "Seymour/Carraher's Polymer Chemistry", Fifth Edition, Revised and Expanded, 2000 Marcel Dekker, Inc., New York—Basel, pp. 270-271.

Lewis, Patti, "Novel Poly(Ester Amide) Scaffold for Wound Management", May 2006 Thesis Presented to Faculty of Graduate School of Cornell University, pp. 1-132.

Katsarava, R. et al. "Amino Acid-Based Bioanalogous Polymers, Synthesis, and Study of Regular Poly(ester amide)s Based on Bis ($\alpha$-amino acid) $\alpha$, $\omega$-Alkylane Diesters, and Aliphatic Dicarboxylic Acids", 1999 J. Poly, Sci.: Part A: Poly, Chem., vol. 37, pp. 391-407.

Koombhongse, Sureeporn et al., "Flat Polymer Ribbons and Other Shapes by Electrospinning", 2001 J. Poly Sci., Part B: Polymer Physics, vol. 39, pp. 2598-2606.

* cited by examiner

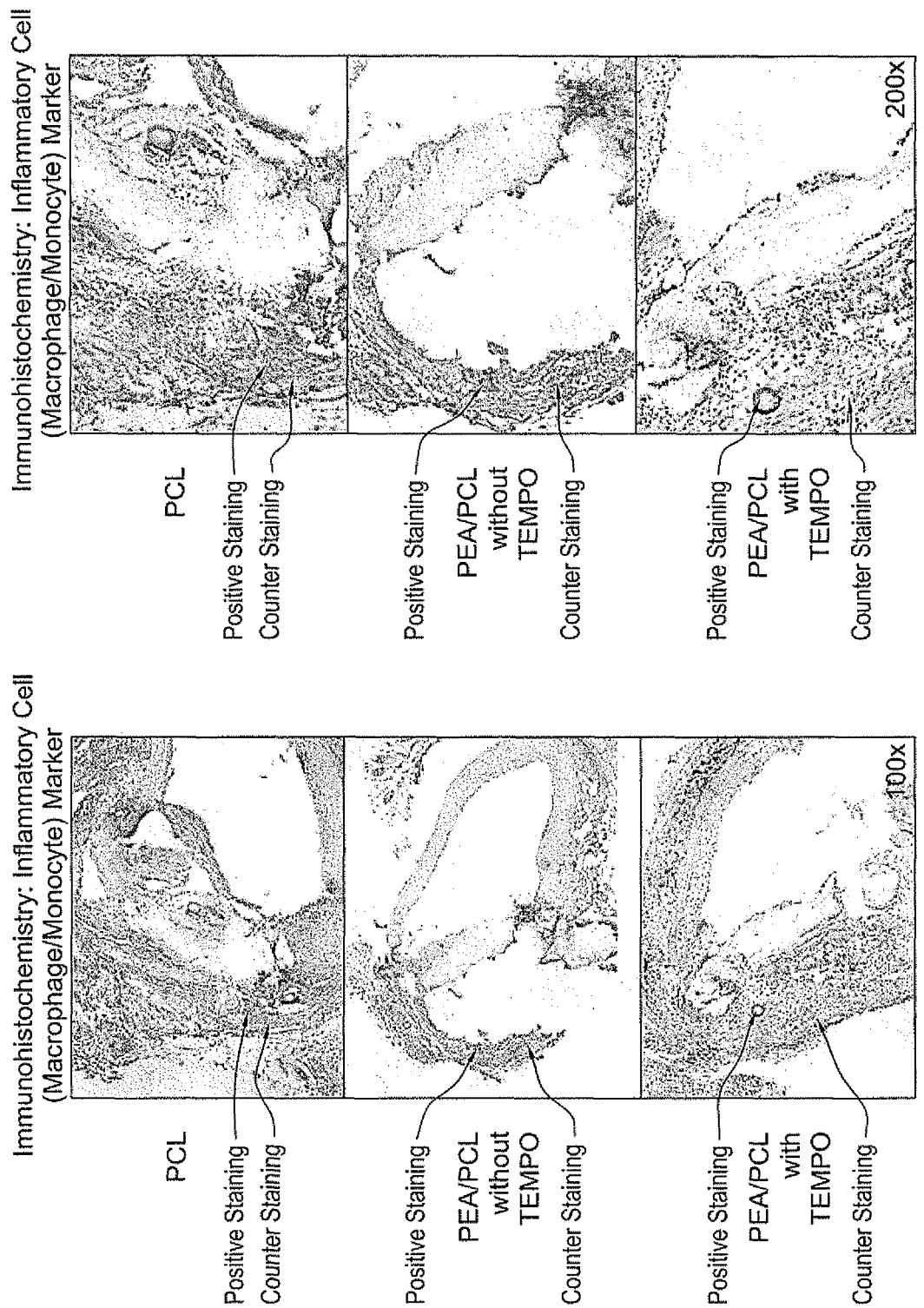

FIBROUS MEMBRANE FOR BIOMEDICAL APPLICATION BASED ON POLY(ESTER-AMIDE)S

CROSS-REFERENCE TO RELATED PATENT APPLICATIONS

This application is a continuation-in-part application of U.S. patent application Ser. No. 11/633,665 filed Dec. 5, 2006, now abandoned. U.S. patent application Ser. No. 11/633,665 claims priority to U.S. Provisional Patent Application No. 60/750,834 filed Dec. 16, 2005. This application also claims priority to U.S. Provisional Patent Application No. 61/064,033 filed Feb. 12, 2008. The entirety of each of the above-identified applications are incorporated herein by reference.

TECHNICAL FIELD

The present invention is directed to poly(ester-amide) structures fabricated for biomedical application.

BACKGROUND OF THE INVENTION

Biodegradable poly(ester-amide)s are known for use for administration of drugs admixed with or chemically linked thereto applied as a drug eluting film or coating and for use in the manufacture of medical devices. See WO 02/18477A2; U.S. Pat. No. 6,503,538; and Katsarava, R., et al., Journal of Polymer Science, Part A, Polymer Chemistry 37, 391-407 (1999). They have not heretofore been fabricated into a form suitable for burn treatment, wound coverage, artificial skin, or scaffolds for tissue engineering.

SUMMARY OF THE INVENTION

It has now been discovered that the field for biomedical application of biodegradable poly(ester-amide)s can be enlarged from the uses previously proposed, by fabricating the biodegradable poly(ester-amides) into fibrous membrane of electrospun fibers. For example, it has been discovered that the poly(ester amide)s as claimed in U.S. Pat. No. 6,503,538 can be fabricated into useful fibrous membranes by electrospinning.

In one embodiment herein, denoted the first embodiment, the invention is directed to a fibrous membrane containing of biodegradable electrospun poly(ester amide), poly(ester urethane), poly(ester urea) or combinations thereof for use for biomedical application, which is sterilizable and has an average fiber diameter ranging from 0.1 to 10 micrometer, e.g., 1.0 to 25.0 micrometer, a median pore size ranging from 0.1 to 100 micrometer, e.g., 2 to 100 micrometers, a surface area ranging from 100 to 300 m$^2$/g, e.g., 150 to 300 m$^2$/g, an average thickness ranging from 0.01 to 0.500 mm, e.g., 0.05 to 0.200 mm, a flexural rigidity ranging from 10 to 80 mg·cm, an average air permeability ranging from 10 to 100 ft$^3$/min/ft$^2$, an average water vapor transmission rate ranging from 200 to 500 g/m$^2$/24 hr, a wettability contact angle ranging from 40 to 80 degrees, e.g., 50 to 80 degrees, tensile stress property ranging from 0.01 to 0.10 kgf/mm$^2$, tensile strain property ranging from 100 to 800%, Young's modulus ranging from 0.20 to 20.0 MPa and tensile toughness ranging from 0.50 to 3.0 MPa.

As used herein the term "biodegradable" means capable of being broken down into innocuous products by various enzymes such as trypsins, lipases and lysosomes in the normal functioning of the human body and living organisms (e.g., bacteria) and/or water environment.

As used herein the term "biomedical application" means application to clinical medicine.

The poly(ester-amide), poly(ester urethane), poly(ester urea) or combinations thereof of the fibrous membrane is preferably one that can be solution electrospun into fibers.

In one aspect of the first embodiment, the poly(ester amide), poly(ester urethane), or poly(ester urea) of the fibrous membrane has a reduced viscosity ranging from 1.0 to 2.0 dL/g, e.g., 1.2 to 2.0 dL/g and is selected from the group consisting of one or more subunits A, and one or more subunits B, and combinations thereof, where the one or more subunits A have the structure

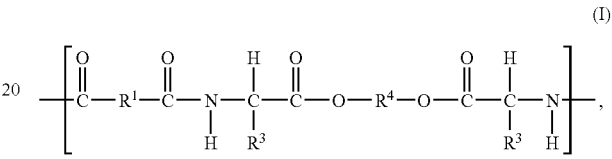

(I)

where R$^1$ is (C$_2$-C$_{20}$) alkylene, R$^3$ is hydrogen, (C$_1$-C$_{20}$) alkyl, (C$_2$-C$_6$) alkenyl, (C$_2$-C$_6$) alkynyl or (C$_6$-C$_{10}$) aryl (C$_1$-C$_6$) alkyl, and R$^4$ is a (C$_2$-C$_{20}$) alkykene, preferably a (C$_2$-C$_{12}$) alkylene, and more preferably (C$_4$-C$_8$ alkylene); and where the one or more subunits B have the structure

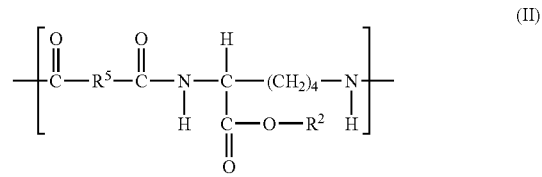

(II)

where R$^2$ is hydrogen or (C$_6$-C$_{10}$) aryl (C$_1$-C$_6$) alkyl and where R$^5$ is (C$_2$-C$_{20}$) alkylene.

In another aspect, the poly(ester amide), poly(ester urethane), or poly(ester urea) of the fibrous membrane has a reduced viscosity ranging from 1.0 to 2.0 dL/g, e.g., 1.2 to 2.0 dL/g and is selected from at least one of a poly(ester amide) (PEA) having a chemical formula described by structural formula (I), Formula (I)

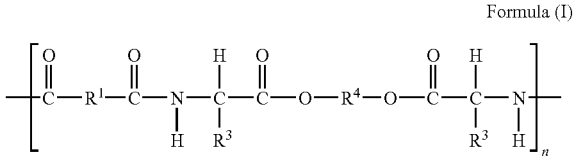

wherein n ranges from about 100 to about 250; R$^1$ is independently selected from residues of (C$_2$-C$_{20}$) alkylene, (C$_2$-C$_{20}$) alkenylene, α,ω-bis(4-carboxyphenoxy) (C$_1$-C$_8$) alkane, 3,3'-(alkanedioyldioxy)dicinnamic acid or 4,4'-(alkanedioyldioxy)dicinnamic acid, or a saturated or unsaturated residues of therapeutic di-acids and combinations thereof; the R$^3$s in individual n monomers are independently selected from the group consisting of hydrogen, (C$_1$-C$_6$) alkyl, (C$_2$-C$_6$) alkenyl, (C$_6$-C$_{10}$) aryl (C$_1$-C$_6$)alkyl, (CH$_2$)$_2$S(CH$_3$), CH$_2$OH, CH(OH)CH$_3$, (CH$_2$)$_4$NH$_2$, (CH$_2$)$_3$NHC(=NH)NH$_2$, 4-methylene imidazole, CH$_2$COOH, (CH$_2$)$_2$COOH, or combinations thereof; and $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of 1,4:3,6-dianhydrohexitols of structural formula (II), saturated or unsaturated therapeutic di-acid residues and combinations thereof;

Formula (II)

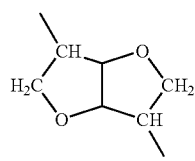

or a PEA having a chemical formula described by structural formula (III):

Formula (III)

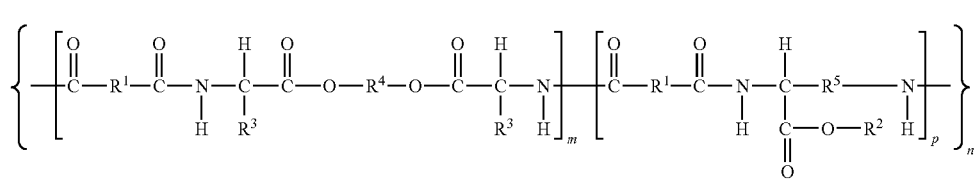

wherein n ranges from about 40 to about 200, m ranges about 0.1 to 0.9: p ranges from about 0.9 to 0.1; wherein $R^1$ is independently selected from residues of $(C_2-C_{20})$ alkylene, $(C_2-C_{20})$ alkenylene, α,ω-bis(4-carboxyphenoxy) $(C_1-C_8)$ alkane, 3,3'-(alkanedioyldioxy)dicinnamic acid or 4,4'-(alkanedioyldioxy)dicinnamic acid, or a saturated or unsaturated residues of therapeutic di-acids and combinations thereof; each $R^2$ is independently hydrogen, $(C_1-C_{12})$ alkyl, $(C_6-C_{10})$ aryl $(C_1-C_6)$ alkyl; the $R^3$s in individual m monomers are independently selected from the group consisting of hydrogen, $(C_1-C_6)$ alkyl, $(C_2-C_6)$ alkenyl, $(C_6-C_{10})$ aryl $(C_1-C_6)$alkyl, $(CH_2)_2S(CH_3)$, $CH_2OH$, $CH(OH)CH_3$, $(CH_2)_4NH_2$, $(CH_2)_3NHC(=NH)NH_2$, 4-methylene imidazole, $CH_2COOH$, $(CH_2)_2COOH$, or combinations thereof; and $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of 1,4:3,6-dianhydrohexitols of structural formula (II), residues of saturated or unsaturated therapeutic diols and combinations thereof; and $R^5$ is independently selected from the group consisting of $(C_1-C_4)$ alkyl, preferably $(CH_2)_4$; or a poly(ester urethane) (PEUR) having a chemical formula described by structural formula (IV), Formula (IV)

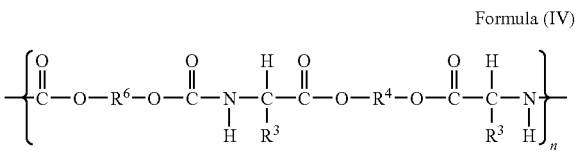

and wherein n ranges from about 100 to about 250; wherein the $R^3$s within an individual n monomer are independently selected from the group consisting hydrogen, $(C_1-C_6)$ alkyl, $(C_2-C_6)$ alkenyl, $(C_6-C_{10})$ aryl $(C_1-C_6)$alkyl, $(CH_2)_2S(CH_3)$, $CH_2OH$, $CH(OH)CH_3$, $(CH_2)_4NH_2$, $(CH_2)_3NHC(=NH)NH_2$, 4-methylene imidazole, $(CH_2COOH$, $(CH_2)_2COOH$, or combinations thereof; $R^4$ and $R^6$ is selected from the group consisting of $(C_2-C_{20})$ alkylene, $(C_2-C_{20})$ alkenylene or $(C_2-C_8)$ alkyloxy $(C_2-C_{20})$ alkylene, and bicyclic-fragments of 1,4:3,6-dianhydrohexitols of structural formula (II) a residue of a saturated or unsaturated therapeutic diol, and mixtures thereof; or a PEUR having a chemical structure described by general structural formula (V), Formula (V)

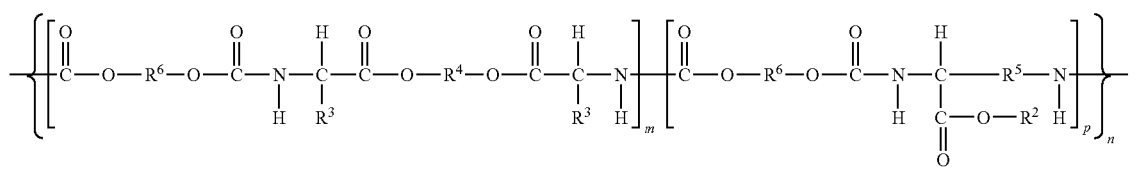

wherein n ranges from about 40 to about 200, m ranges about 0.1 to about 0.9: p ranges from about 0.9 to about 0.1; each $R^2$ is independently hydrogen, $(C_1-C_{12})$ alkyl, $(C_6-C_{10})$ aryl $(C_1-C_6)$ alkyl; the $R^3$s within an individual m monomer are independently selected from the group consisting of hydrogen, $(C_1-C_6)$ alkyl, $(C_2-C_6)$ alkenyl, $(C_6-C_{10})$ aryl $(C_1-C_6)$alkyl, $(CH_2)_2S(CH_3)$, $CH_2OH$, $CH(OH)CH_3$, $(CH_2)_4NH_2$, $(CH_2)_3NHC(=NH)NH_2$, 4-methylene imidazole, $CH_2COOH$, $(CH_2)_2COOH$, or combinations thereof; $R^4$ and $R^6$ is independently selected from $(C_2-C_{20})$ alkylene, $(C_2-C_{20})$ alkenylene or $(C_2-C_8)$ alkyloxy $(C_2-C_{20})$ alkylene, bicyclic-fragments of 1,4:3,6-dianhydrohexitols of structural formula (II), a residue of a saturated or unsaturated therapeutic diol, and mixtures thereof; and $R^5$ is independently selected from the group consisting of $(C_1-C_4)$ alkyl, preferably $(CH_2)_4$; or a poly(ester urea) (PEU) having a chemical formula described by structural formula (VI),

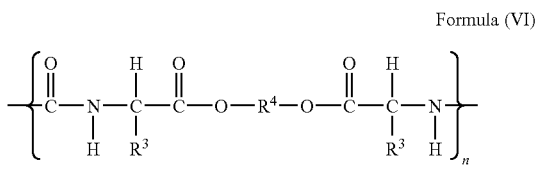

Formula (VI)

wherein n is about 100 to about 250; the $R^3$s within an individual n monomer are independently selected from hydrogen, $(C_1-C_6)$ alkyl, $(C_2-C_6)$ alkenyl, $(C_6-C_{10})$ aryl $(C_1-C_6)$alkyl, $(CH_2)_2S(CH_3)$, $CH_2OH$, $CH(OH)CH_3$, $(CH_2)_4NH_2$, $(CH_2)_3NHC(=NH)NH_2$, 4-methylene imidazole, $CH_2COOH$, $(CH_2)_2COOH$, or combinations thereof; $R^4$ is independently selected from $(C_2-C_{20})$ alkylene, $(C_2-C_{20})$ alkenylene, $(C_2-C_8)$ alkyloxy $(C_2-C_{20})$ alkylene, a residue of a saturated or unsaturated therapeutic diol, or a bicyclic-fragment of a 1,4:3,6-dianhydrohexitol of structural formula (II) and combinations thereof;

or a PEU having a chemical formula described by structural formula (VII),

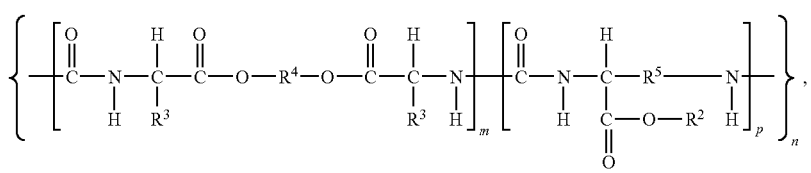

Formula (VII)

wherein m is about 0.1 to about 1.0; p is about 0.9 to about 0.1; n is about 40 to about 200; each $R^2$ is independently hydrogen, $(C_1-C_{12})$ alkyl, or $(C_6-C_{10})$ aryl $(C_1-C_6)$ alkyl; and the $R^3$s within an individual m monomer are independently selected from hydrogen, $(C_1-C_6)$ alkyl, $(C_2-C_6)$ alkenyl, $(C_6-C_{10})$ aryl $(C_1-C_6)$alkyl, $(CH_2)_2S(CH_3)$, $CH_2OH$, $CH(OH)CH_3$, $(CH_2)_4NH_2$, $(CH_2)_3NHC(=NH)NH_2$, 4-methylene imidazole, $CH_2COOH$, $(CH_2)_2COOH$, or combinations thereof; $R^4$ is independently selected from $(C_2-C_{20})$ alkylene, $(C_2-C_{20})$ alkenylene, $(C_2-C_8)$ alkyloxy $(C_2-C_{20})$ alkylene, a residue of a saturated or unsaturated therapeutic diol; or a bicyclic-fragment of a 1,4:3,6-dianhydrohexitol of structural formula (II), or a mixture thereof; and $R^5$ is independently selected from the group consisting of $(C_1-C_4)$ alkyl, preferably $(CH_2)_4$.

For purposes of scaffold for tissue engineering, the poly (ester-amide) of the fibrous membrane, in one case has the structure (I) where $R^1$ is $(CH_2)_8$, $R^3$ is

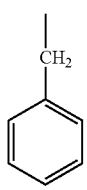

and $R^4$ is $C_4-C_8$ alkylene.

The poly(ester-amide) within the preferred case described above, determined to be most preferred of the poly(ester-amide)s tested, for a scaffold for tissue engineering, has the structure

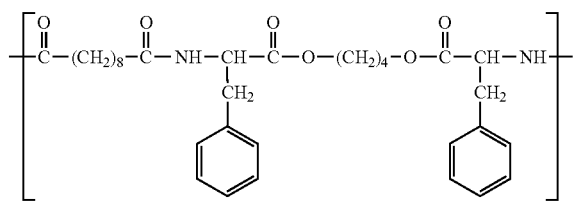

Suitability for a scaffold for tissue engineering is shown by cell attachment and proliferation in a Calcein-AM assay of cells seeded on the fibrous membrane. The seeding and assay for cell attachment and proliferation are described below. Calcein-AM is available from Molecular Probes (Eugene, Oreg.). The cells used as model cells to show attachment and proliferation were keratinocytes, particularly Normal Human Epidermal Keratinocyte cell line (NHEK cell line), Catalog No. CC-2501 from Cambrex Bio Science Walkersville, Inc. (Walkersville, Md.) or Biolife Solutions, Inc. (Oswego, N.Y.). These cells were chosen for testing because of easy availability and ease of manipulation. This testing is relevant to use for a scaffold for tissue engineering because tissue engineering involves seeding of cells into a scaffold for proliferation into tissues.

Other utilities for the fibrous membranes herein are burn treatment including adjunct therapy for burn treatment, wound coverage, partial thickness wound repair, healing acceleration, artificial skin, barrier to prevent tissue adhesions after surgery and administration of drugs or other agent physically or chemically associated therewith, for these purposes.

The fibrous membranes herein are advantageous over films of the same poly(ester-amide) in providing a three dimensional porous network structure that a two dimensional film does not have.

So far as scaffolds for tissue engineering are concerned, the fibrous membranes herein are advantageous over films of the same poly(amide-ester) because they have a larger surface area for the cells to attach to and proliferate.

So far as utility for administration of drug or other agent is concerned, the drug or other agent, e.g., drug or other agent is matrixed into the fibrous membrane, or attached to the fibrous membrane.

We turn now to determination of the various properties of the fibrous membranes herein.

Sterilizability is determined as follows: Samples of fibrous membranes are cut to the size of the bottoms of wells of a 96-well microplate (¼ inch). For example, the samples are attached around the bottom edges with 15% in chloroform solution. A microplate with samples therein is placed into a Medi-Plus ethylene oxide bag, the bag is sealed and air plasma sterilization is carried out using a Harrick Plasma Cleaner model PDC-32G (Harrick Scientific, NY) on high setting for five minutes.

Fiber diameter and pore size are determined as follows based on scanning electronmicroscopy (SEM) pictures using Scion Image for Windows (www.scioncorp.com/pages/scionimagewindows.htm): Pore size of nonwoven and average fiber diameter are measured from the SEM images using the Scion program. For example, electrospun fibrous poly(ester-amide) mats are sputter coated with gold for thirty seconds using a BAL-TEC sputter coater (Manchester, N.H.) (Bal-Tech SCD050), and the sputter coated mats are observed using a Hitachi S4500 (Mountain View, Calif.) scanning electron microscope and an accelerating voltage of 10 kV.

Surface area is determined as follows: Surface area is analyzed using a Brunauer, Emmett and Teller (BET) surface area analyzer from Porous Materials, Inc. (Ithaca, N.Y.). For example, a poly(ester amide) sample is cut and weighed and is then placed in a BET tube. The test is run at −195.76° C. with adsorbate nitrogen gas entering the system at 20 microns/minute under vacuum. One mat is used for providing all the samples for obtaining average surface area data.

Thickness is determined according to ASTM D1777-96 as follows: Measurements are carried out using a Sherman W. Frazier Compressometer using a circular, 9.525 mm diameter presser foot. Ten measurements are made at a pressure of 0.023 MPa (3.4 pounds per square inch) to obtained an average value.

Flexural rigidity is measured according to ASTM D1388 as follows: Standard commercially available spun bonded polypropylene (40 GMS, i.e., 40 gms per square meter) nonwoven samples are cut into 6×1 inch strips. Poly(ester amide) constructs are cut into 3×1 inch strips. The strips are mounted on a horizontal platform with one end sloping at a 45 degree angle. Each strip is slowly pushed off the platform in such a way that it overhangs. The fabric bends down and from the length and weight per square centimeter, the flexural rigidity G (stiffness) is calculated according to the following equation.

$$G = W \times c^3$$

where W=mg/cm$^2$ (the weight per unit area) and c is the bending length—the length of overhang in cm/2. The flexural rigidity of the spun bonded polypropylene is used as a control. The units are denoted with the terminology mg·cm. Five measurements are made to obtain an average value.

Air permeability is measured according to ASTM D737-96 as follows: Circular samples with a minimum diameter of 3.5 inches are mounted on a Frazier precision instrument (Silver Spring, Md.). The rate of airflow through the fabric is measured under a differential pressure range of 0-1.0 inches of water. The data is expressed in ft$^3$ air/min/ft$^3$. The air permeability of spun bonded 40 GSM polypropylene nonwoven material is used as a control. Five measurements are made to obtain an average value.

Water vapor transmission rate is determined according to ASTM D6701-01 as follows: Samples are cut into 2.5 inch diameter circles and weighed to obtain sample density (gms/m$^2$)·10 mL of distilled water is placed into the bottom of model 305 water vapor permeability cups. Then the samples are mounted onto the cups. Each assembled system including cup, fabric and water is weighed at 0, 0.5, 1, 3, 5, 12, 24 and 48 hours. The test is performed at 21° C. and 65% relative humidity. Three measurements are made to obtain an average value for water vapor transmission rate (water vapor permeability). The water vapor transmission rate is calculated according to the equation (G/t)A where G is the weight change in grams, t is the time during which G occurred, in hours, and A is the test area (cup's mouth area) in m$^2$. The results are expressed in grams moisture/m$^2$ fabric/24 hours. The water vapor transmission rate of spunbonded polypropylene 40 GSM nonwoven, is used as a control.

Wettability contact angle of each poly(ester amide), poly(ester urethane), polyester urea). For example, film of each poly(ester amide) is cast by pouring a layer of approximate thickness of 0.500 mm of 7% weight/weight, poly(ester-amide) in chloroform solution, onto a Teflon® plate. When a uniform thickness layer is obtained, the plate is covered by a watch glass to decrease evaporation rate. Each film layer is dried at room temperature for twenty-four hours. After the twenty-four hour drying time, each film is pulled from its Teflon® plate and cut into three 0.5 inch by 0.5 inch samples. The samples are mounted onto the contact angle analyzer (Hingham, Mass.) stage with double sided tape. Each stage is inserted into the analyzer and a small amount of distilled water or methylene iodide ($CH_2I_2$) is dropped onto the sample and brought into the viewing area. The height and ½ the width of the droplet are measured and the contact angle is calculated according to the following equation:

$$\cos\theta = \frac{x^2 - y^2}{x^2 + y^2} \text{ where}$$

x=½ drop width, y=drop height, θ=contact angle.

Tensile properties are determined as follows: Tensile stress, tensile strain, Young's modulus and tensile toughness of poly(ester amide) and spunbonded 40 GSM polypropylene are measured. The samples are cut into 1×6 cm rectangular shapes and are mounted with vertical orientation in an Instron testing machine, model 1166. Tests are performed using a gauge length of 50 mm and a cross-head speed of 50 mm/minute. Average fabric thickness is used for calculating the tensile properties. The strength of a spunbonded polypropylene 50 GSM nonwoven material is used as a control. Five specimens are tested to obtain the average tensile properties.

Biodegradability is determined by in vitro α-chymotrypsin catalyzed hydrolysis as described in Katsarava, R., et al., Journal of Polymer Science: Part A. Polymer Chemistry 37, 391-407 (1999).

Reduced viscosities are determined with a capillary viscometer.

For example, each poly(ester amide) (PEA) polymer is dissolved with m-cresol to a 0.25 g/dL concentration. After the PEA polymers are dissolved, the solution is poured into a model C572 Glass Cannon capillary viscometer. The capillary viscometer is placed into a VWR Scientific Model 1120 Constant Temperature Circulator and the temperature held constant at 25 degrees Celsius. Suction is applied to the solution until it is past the top mark. Once the solution flows past the mark, timed collection is started. The timed collection is ended when the solution passes the second mark. The procedure is repeated 5 times for the pure solvent (m-cresol) and each polymer solution. The reduced viscosity is calculated using the following equations.

$$\eta = \eta_s/\eta_9 \quad \text{Equation 1}$$

$\eta_s$=solution time (seconds)
$\eta_9$=m-Cresol time (seconds)

$$\eta_{sp} = \eta - 1 \quad \text{Equation 2}$$

$$\eta_{reduced} = \eta_{sp}/\text{concentration}(0.25 \text{ g/dL}) \quad \text{Equation 3}$$

REFERENCE

Jan F. Rabek, "Experimental methods in polymer chemistry", Wiley-Interscience, NY, 1980, Chapter 9 "Viscosimetric methods", pp. 123-136.

In another embodiment herein, denoted the second embodiment, the fibrous membrane of the first embodiment is made by a method comprising solution electrospinning of poly(ester-amide), polyester urethane), poly(ester urea) or combinations thereof and varying thickness of the fibrous membrane and/or solution concentration and/or collection distance and/or voltage and/or fiber diameter to vary pore size.

In yet another embodiment, denoted the third embodiment, a therapeutically effective amount of a compound for accelerating wound healing, enhancing burn treatment or providing adjunct therapy for burn treatment is incorporated into the fibrous membrane. For example, the compound may be gallium nitrate or 2,2,6,6-tetramethylpiperidine-1-oxy radical.

BRIEF DESCRIPTION OF THE DRAWINGS

FIGS. 14(a) and (b) shows the results of an immunohistochemistry analysis with inflammatory cell markers at 100× and 200× magnification, respectively.

DETAILED DESCRIPTION

Figure 1A:
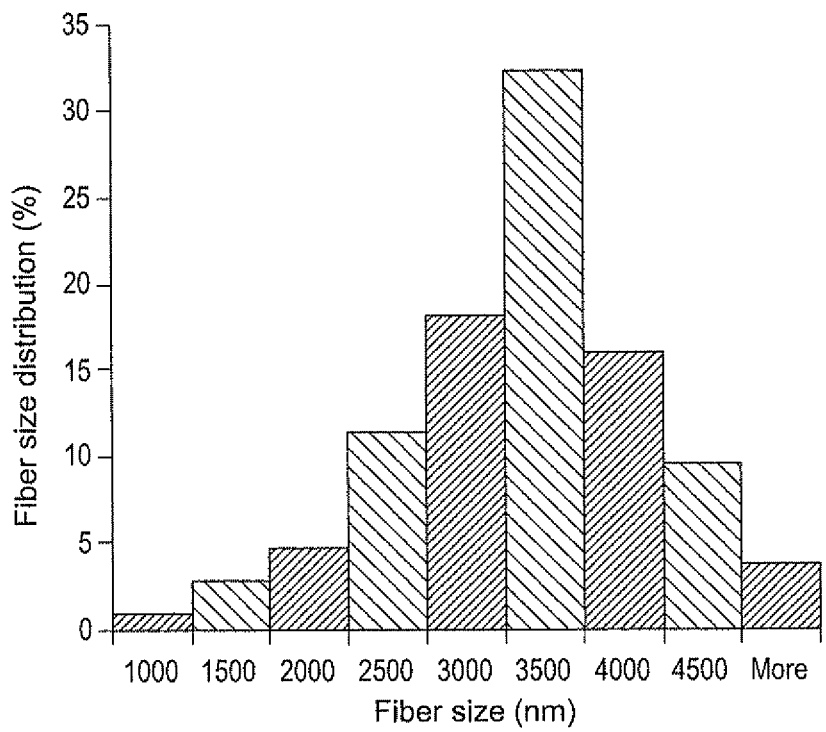
FIG. 1 fiber size distribution of 8-Phe-4 fibers electrospun from (a) chloroform and (b) a mixture chloroform and DMF.

The polymerizations to provide the poly(ester-amide), poly(ester urethane), poly(ester urea) or combinations thereof can be made by a variety of techniques including by an interfacial technique or by active polymerization.

The poly(ester-amide)s described above, can be prepared by active polymerization as described in Katsarava, R., et al., Journal of Polymer Science: Part A: Polymer Chemistry 37, 391-407 (1999); U.S. Pat. No. 6,503,538; and in WO 02/18477A2.

We turn now to the interfacial technique. This is described at pages 270-271 of Seymour/Carraher's Polymer Chemistry, Fifth Edition (2000) which is incorporated herein by reference. Description of the technique there includes the following "Many of the reactions can be carried out under essentially nonequilibrium conditions. The technique is heterophasic, with two fast-acting reactants dissolved in a pair of immiscible liquids, one of which is usually water. The aqueous phase typically contains the Lewis base—a diol, diamine or dithiol—along with any added base or other additive. The organic phase consists of a Lewis acid, such as an acid chloride, dissolved in suitable organic solvent, such as toluene, octane or pentane. Reaction occurs near the interface."

For example, the poly(ester-amide)s made for testing herein are as follows:

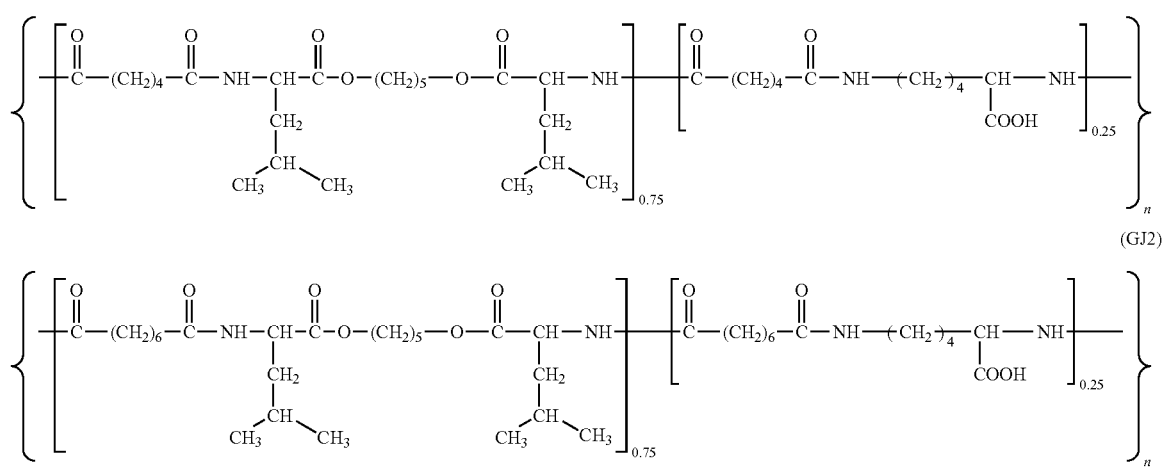

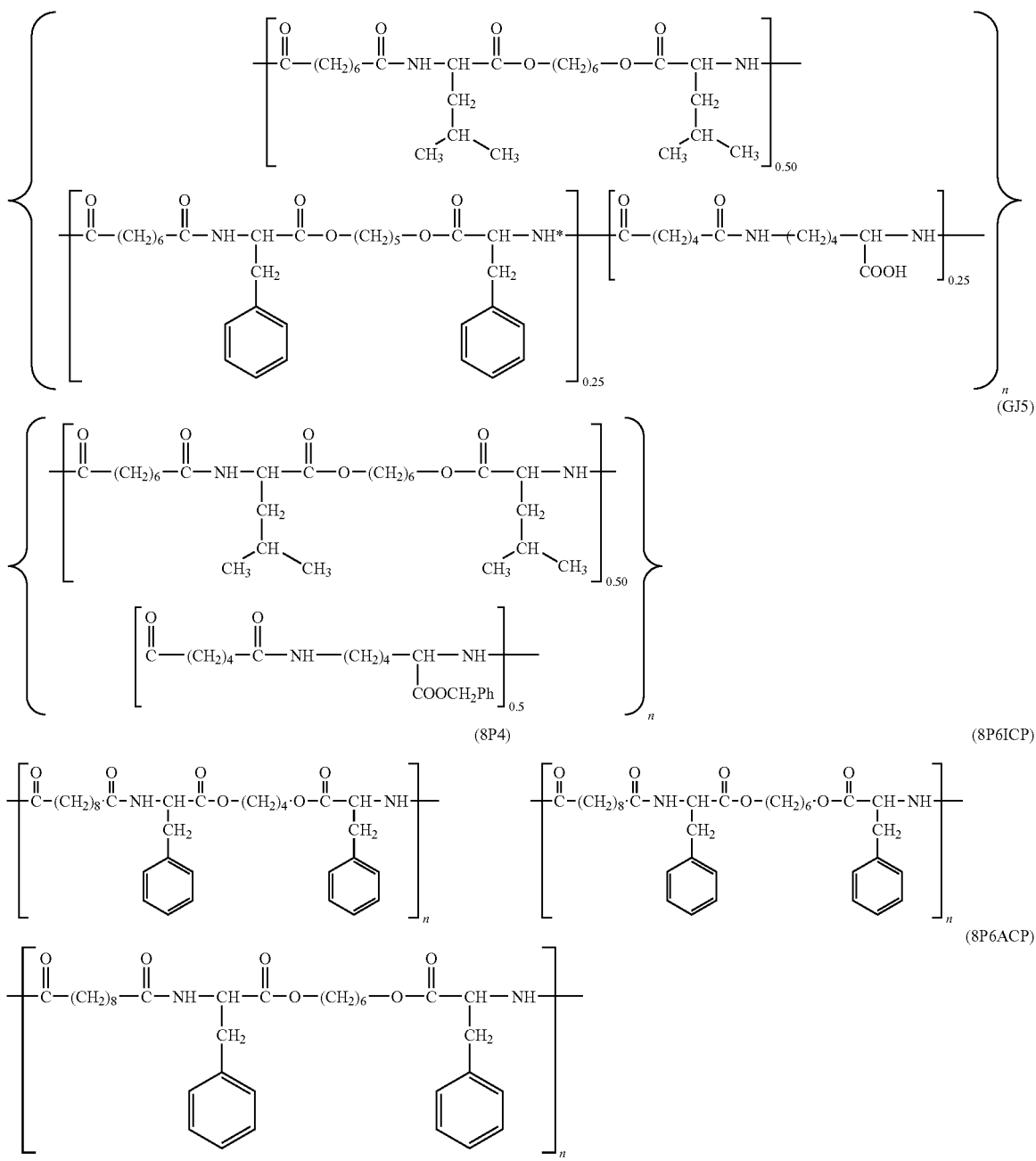

GJ1, GJ2, GJ4 and GJ5 were synthesized with the lysine unit being in the benzyl ester form. For GJ1 and GJ2, the benzyl ester of the lysine unit was more than 90% converted by hydrogenolysis to the free acid form for electrospin processing. For GJ4, 40% of the benzyl ester in the lysine unit was converted by hydrogenolysis to the free acid form for electrospin processing. GJ5 was left entirely with the lysine unit in the benzyl ester form for electrospin processing.

GJ1, GJ2, GJ4 and GJ5 were made by active polymerization.

(8P4) and (8P6 ACP) were made by active polymerization.

(8P4 ICP) was made by the interfacial technique.

Reduced viscosities for the above are set forth in Table 1 below.

TABLE 1

| Structure | $\eta_{red}$ (dL/g) |
| --- | --- |
| GJ1 | 1.698 |
| GJ2 | 1.571 |
| GJ4 | 1.616 |
| GJ5 | 1.415 |
| 8P4 | 1.433 |
| 8P6 ICP | 1.768 |
| 8P6 ACP | 1.554 |

The molecular weight can be determined from the reduced viscosities.

We turn now to electrospinning of the poly(ester-amide), poly(ester urethane), poly(ester urea) or combinations thereof into fibers and formation of fibrous membrane.

Solution or melt electrospinning can be used.

Described below is the lab set up for the fibrous membrane production herein by solution electrospinning. However, any solution electrospinning system including conventional ones can be used, such as electrospinning device using a syringe pump, syringe, collection plate, and high voltage device.

For admixture of drug or other agent in the fibrous membrane, for example, drug or other agent that accelerates wound healing, the drug or other agent can be incorporated into polymer solution or attached to a polymer prior to solution electrospinning.

In the experiments carried out, polymer solutions were placed in a horizontally oriented 5 cc glass syringe fitted with a 24 gauge blunt end needle. The collection plate was a wire mesh taped to three layers of wax paper on the collecting face. The wire mesh was connected to a grounding wire and was positioned 10-15 cm from the needle. The voltages applied to the needle ranged from 9 to 20 kV. Flow rates tried ranged from 0.01 mL/min to 0.10 mL/min. Preferred conditions determined were 0.02 mL/min flow rate, 15 cm distance between needle end and collection plate and 11 kV voltage applied to the needle.

Droplets are formed at the needles end. The charge on the needle provides an electric charge in the droplets emitting therefrom to overcome the surface tension of a droplet to produce a jet of polymer giving rise to unstable flow toward the collecting plate manifested by a series of electrically induced bending instabilities/whipping motions and evaporation of solvent and production of elongated polymer fibers and deposit thereof on the wax paper of the collection plate as a fibrous membrane of the polymer.

The solvent selected for dissolving a poly(ester-amide), poly(ester urethane), poly(ester urea) or combinations thereof for the solution electrospinning should provide dissolution within 24 hours at room temperature and solution viscosity and evaporation rate suitable to produce fiber by solution electrospinning. A solution viscosity of 1-20 poise, a surface tension for the solution of 33-35 dyne/sm and a solvent evaporation rate of at least 1.0 $g/m^2/h$ are aimed for.

Since comparative data was being determined, a solvent was sought that would dissolve all seven specific poly(ester-amide)s in 24 hours at room temperature. This criterion was found to be met by both dimethylformamide (DMF) and chloroform. Chloroform was selected for use in experiments because it produced higher viscosity poly(ester-amide) solutions compared to an equal concentration of the same poly(ester-amide) in DMF and a higher evaporation rate so that fibers would more likely solidify and dry before reaching the collection plate.

The most uniform poly(ester-amide) fibers were observed at 12.5, 15% and 17% concentration of poly(ester-amide) in chloroform and 15% and 17% were chosen for further test work.

GJ1 was not able to be solution electrospun. It would not form fibers and the solution would just create spray droplets. However, it may be able to be melt electrospun.

GJ4 provided the best solution electrospinning results—a single thin filament pulled out of the droplet during electrospinning.

In the experiments carried out, the poly(ester-amide) fibrous membranes obtained had average fiber diameter ranging from 2.0 to 25.0 micrometers, and preferably 2 to 20 micrometers, a median pore size of 50 micrometer, a surface area of 220 $m^2/g$, an average thickness of 0.1 mm, a flexural rigidity ranging from 4 to 65 mg·cm, an average air permeability ranging from 25 to 90 $ft^3/min/ft^2$, an average water vapor transmission rate ranging from 280 to 430 $g/m^2/hr$, a wettability contact angle ranging from 60 to 75 degrees, tensile stress property ranging from 0.035 to 0.095 $kgf/mm^2$, tensile strain property ranging from 125 to 795%, Young's modulus ranging from 0.9 to 14.5 MPa and tensile toughness ranging from 0.90 to 2.10 MPa.

Pore size can be varied by varying thickness of the fibrous membrane. The greater the thickness, the smaller the pore size. Increasing the solution concentration causes increase in fiber diameter. Fiber diameter is related to collection distance. For example, in experiments carried out on poly(ester amide) 8P4, electrospun at 15% concentration in solution, use of a collection distance of 15 cm created fiber diameter of 2 µm whereas use of a collection distance of 10 cm created a fiber diameter of 2.35 µm. At 20 cm, the fiber diameter becomes larger because the collection plate is beginning to be moved outside the electrical charge field resulting in lesser force to draw the fiber to its fall extension. Thus, the collection distance had an initial inverse effect on fiber diameter as the collection distance increased. Fiber diameter increases with voltage increase. In experiments carried out on poly(ester amide) 8P4 at 15% concentration in solution at voltage levels of 9, 11, 15 and 20 kV, as applied voltage was increased, the fiber diameter first is increased and then is decreased and number of bead defects increased with increasing voltage. Variation in fiber diameter can be used to vary porosity. For a given coverage, $g/m^2$, increase in fiber diameter can provide increase or decrease in pore size.

Testing for cell attachment and proliferation (tissue engineering scaffold utility) was carried out as follows:

Firstly, all seeding was carried out as follows: Normal human epidermal keratinocytes (NHEK cells) were plated in a monolayer in 75 $cm^2$ tissue culture flask and cultured till the cells reached three passages. After the third passage, the cells were removed by trypsin treatment, counted, and seeded onto the constructs at a density of 10,000 cells/well. The constructs were maintained in an incubator at 37° C. with 5% $CO_2$. The medium was changed every three days.

Cell attachment as a result of seeding was determined as follows:

To assay the cells attached, the medium was removed and wells were rinsed with Hanks Balanced Salt Solution (HBSS) without $Mg^{2+}$, $Ca^{2+}$, and phenol red. The constructs were exposed to a Calcein-AM solution (1:250 HBSS without phenol red) for thirty minutes. Cell numbers were indicated directly by the relative fluorescence units (RFU) obtained from a Spectrafluor. Calcein-AM fluorescent pictures were obtained by Zeiss optical fluorescent microscope.

To determine cell proliferation, the cells were assayed at day 1, 3 and 7. A Spectrafluor and Zeiss optical fluorescent microscope collected the readings.

Of the poly(ester amide)s specifically described above, 8P4 was considered the model for fibrous membranes production and the following results were obtained on fibrous membranes from 8P4.

Results are set forth below:

For fibrous membranes from 8P4 from electrospinning from 15% concentration at feed rate 0.02 mL/min, 11 kV, 10 cm collection distance, absorbencies (RFU) denoting cell proliferation were 14,000, 18,000 and 31,000 at days 1, 3 and 7 as compared to absorbencies of 22,000, 26,000 and 44,000 for a well with only NHEK cells and no scaffold.

The fibrous membranes from 8P4 from electrospinning at feed rate of 0.02 mL/min, 11 kV and 10 cm collection distance had properties as follows: Average fiber diameter of 3 micrometers, median pore size of 50 micrometers, a surface area of 220 m²/g, an average fabric thickness of 0.102 mm, a flexural rigidity of 19.5 mg·cm, an air permeability of 31.8 ft³/min/ft², an average water vapor transmission rate of 427 g/m^{2/24} hr, a wettability content angle of 66.4 degrees, tensile stress of 0.073 kgf/mm², tensile strain of 144.5%, Young's modulus of 14.31 MPa, and tensile toughness of 0.902 MPa.

As indicated above, the fibrous membranes herein can incorporate drug or other agent.

Examples of these are fibrous membranes incorporating agent for accelerating wound healing or for burn treatment or adjunct therapy for burn treatment (e.g., gallium nitrate), for administration of nitroxyl radical (e.g., 2,2,6,6-tetramethylpiperidine-1-oxy radical), e.g., to reduce intimal hyperplasia in vascular grafts or to reduce tissue adhesion by retarding smooth muscle cell proliferation, or for administration of rapamycin (e.g., sirolimus) to prevent tissue adhesion after abdominal or other surgery, or for administration of therapeutic protein (as suggested by incorporation into the fabric of the model protein albumin).

In one embodiment, a therapeutically effective amount of the drug or agent is a NO derivative compound that binds to the carboxylic acid of the starting polymer. Examples of such compounds are 2,2,5,5-tetramethylpyrrolidine-1-oxy; 2,2,5,5-tetramethyl-3-pyrroline-1-oxy-3-carbonyl; 4-(N,N-dimethyl-N-hexadecyl)ammonium-2,2,6,6-tetramethylpiperidine-1-oxy, iodide (CAT16); 4-trimethylammonium-2,2,6,6-tetramethylpiperidine-1-oxy, iodide (CAT 1); 3-amino-2,2,5,5-tetramethylpyrrolidine-1-oxy; N-(3-(iodoacetyl)amino)-2,2,5,5-tetramethylpyrrolidine-1-oxy (PROXYL 1A); succinimidyl 2,2,5,5-tetramethyl-3-pyrroline-1-oxy-3-carboxylate; 2,2,5,5-tetramethyl-3-pyrroline-1-oxy-3-carboxylic acid; 2,2,6,6-tetramethylpiperidine-1-oxy; 4-amino-2,2,6,6-tetramethylpiperadine-1-oxy; 4-carboxy-2,2,6,6-tetramethylpiperadine-1-oxy; 4-acetamido-2,2,6,6-tetramethylpiperadine-1-oxy; 4-bromo-2,2,6,6-tetramethylpiperadine-1-oxy; 4-(N,N-dimethyl-N-(2-hydroxyethyl))ammonium-2,2,6,6-tetramethylpiperidine-1-oxy; 4-(N,N-dimethyl-N-(3-sulfopropyl)ammonium-2,2,6,6-tetramethylpiperidine-1-oxy; N-(4-(iodoacetyl)amino-2,2,6,6 tetramethylpiperidine-1-oxy; N-(2,2,6,6-tetramethylpiperidine-1-oxy-4-yl)maleimide; and mixtures thereof. A particularly preferred compound is 4-amino-2,2,6,6-tetramethylpiperadine-1-oxy radical.

The drug or agent may be present in a fibrous membrane in an amount of 0.1 to 50%, 0.1 to 30%, 0.1 to 15%, 0.1 to 10%, 0.1 to 5.0%, or 0.1 to 2.5%, 1.0 to 50%, 1.0 to 30%, 1.0 to 15%, 1.0 to 10%, 1.0 to 5.0%, or 1.0 to 2.5% by weight of the poly(ester urethane), poly(ester urea) or combination thereof.

In yet another embodiment, the fibrous membranes contain more than one drug or agent.

In one embodiment, a fibrous membrane containing a drug or agent is produced that possesses properties similar to the fibrous membranes discussed above. For example, the fibrous membranes contain a biodegradable electrospun poly(ester amide), poly(ester urethane), poly(ester urea) or combinations thereof for use for biomedical application, which is sterilizable and has an average fiber diameter ranging from 0.01 to 25.0 micrometers, 0.01 to 10.0 micrometers, 0.01 to 1.0 micrometers, 0.01 to 1.0 micrometers, or 0.1 to 1.0 micrometers, or 0.25 micrometers to 0.75 micrometers. The biodegradable electrospun poly(ester amide), poly(ester urethane), poly(ester urea) or combinations thereof has a volume ratio of drug or agent of (e.g., 2,2,6,6-tetramethylpiperadine-1-oxy radical) to poly(ester amide) of 0.01-1.0:1.0, and more preferably 0.1-1.0:1.0.

The fibrous membranes containing a drug or agent (e.g., 2,6,6-tetramethylpiperadine-1-oxy radical) may be produced with the methods discussed above. For example, a solution containing poly(ester-amide), poly(ester urethane), poly(ester urea) or combinations thereof, and drug or agent is prepared with a solvent, such as dichloromethane (DCM), dimethylformamide (DMF), chloroform, or a mixture thereof. When a mixture of chloroform and DMF is used, the ratio of chloroform to DMF is preferably 1.8-2.2 to 1.0, and more preferably 2.0:1.0. The feed volume ratio of drug or agent (e.g., 2,2,6,6-tetramethylpiperadine-1-oxy radical) to poly(ester amide), poly(ester urethane), poly(ester urea) or combinations thereof is 0.01-1.0:1.0, preferably 0.05-0.5:1.0, and more preferably 0.1-1.0:1.0.

Prior to electrospinning, a second biodegradable polymer may be added to the solution. In one embodiment, the second biodegradable polymer is a biodegradable aliphatic polyester. The weight average molecular weights of these biodegradable aliphatic polyesters typically range from 10,000 to 500,000, and preferably from 20,000 to 125,000.

Examples of biodegradable aliphatic polyesters include polyglycolic acids, poly-L-lactides, poly-D,L-lactides, poly-3-hydroxy butyrate, polyhydroxyvalerate, polycaprolactones, poly(epsilon-caprolactone), modified poly(alpha-hydroxyacid)homopolymers (e.g., a homopolymer of the cyclic diestermonomer), 3-(S)[alkyloxycarbonyl)methyl]-1,4-dioxane-2,5-dione (which has the formula 4 where R is lower alkyl, depicted in Kimura, Y., "Biocompatible Polymers" in Biomedical Applications of Polymeric Materials, Tsuruta, T., et al, eds., CRC Press, 1993 at page 179), glycolide-lactide copolymers, glycolide-caprolactone copolymers, poly-3-hydroxy butyrate-valerate copolymers, 3-(S)[(alkyloxycarbonyl)methyl]-1,4-dioxane-2,5-dione, 3-(S)[(alkyloxycarbonyl)methyl]-1,4-dioxane-2,5-dione with L-lactide, and poly (glycolide-L-lactide) copolymers.

In one embodiment, the poly(glycolide-L-lactide) may be formed utilizing a mole ratio of glycolic acid to L-lactic acid ranging from 5:95 to 95:5 and preferably a mole ratio of glycolic acid to L-lactic acid ranging from 45:65 to 95:5, e.g., a mole ratio of glycolic acid to L-lactic acid of 90:10 or a mole ratio of glycolic acid to L-lactic acid of 50:50. The glycolide-caprolactone includes glycolide and epsilon-caprolactone block copolymers (e.g., monocryl or poliglecaprone).

The second biodegradable polymer is added to the electrospinning solution in an amount of 10-90% by weight 20-80% by weight, 30-70% by weight, 40-60% by weight, or 45-55% by weight of the poly(ester-amide), poly(ester urethane), poly(ester urea) or combinations thereof and second biodegradable polymer.

Fibrous membranes containing a drug or agent are made by a method comprising solution electrospinning of poly(esteramide) and drug or agent as discussed above. Approximately 75-100%, preferably 90-100%, and more preferably 95-100% of drug or agent in solution are impregnated or loaded into the finished fibrous membrane.

In yet another embodiment, a drug or agent is chemically conjugated or bonded to a poly(ester-amide), poly(ester urethane), poly(ester urea) or combinations thereof with a conjugating agent (e.g., 1,1'-carbonyldimidazole) prior to electrospinning. For example, the drug or agent may be attached or bonded to poly(ester-amide) in accordance with U.S. Pat. Nos. 7,208,018, 7,304,122, 6,503,538, and 5,516,881. The degree of attachment of the drug or in the resulting polymer varies from 75-100%, preferably 90-100%, and more preferably 95-100% as determined by UV spectrophotometry in ethanol solution at 250 nm (polymer does not absorb at this wavelength).

The resulting polymer can then be made by a method comprising solution electrospinning as discussed above.

For example, solution for electrospinning may be obtained with a solvent of DCM, DMF, chloroform, or a mixture thereof. When a mixture of chloroform and DMF is used, the ratio of chloroform to DMF is preferably 1.8-2.2 to 1.0, and more preferably 2.0:1.0. The feed volume ratio of drug or agent is 0.01-1.0:1.0, and preferably 0.1-1.0:1.0. A second biodegradable polymer may also be added to a solution containing a chemically conjugated drug or agent in a similar manner as discussed above.

The fibrous membranes containing a biodegradable electrospun poly(ester amide), poly(ester urethane), polyester urea) or combinations thereof comprising an impregnated or attached drug or agent degrade a 1.25 to 4.0 times, and preferably 1.5 to 3.0 times more quickly than a film containing the same material as determined by in vitro α-chymotrypsin catalyzed hydrolysis as described in Katsarava, R., et al., *Journal of Polymer Science: Part A*. Polymer Chemistry 37, 391-407 (1999).

In fibrous membranes impregnated with a drug or agent, the drug or agent is released into a medium as degradation of the fibrous membrane occurs and/or by diffusion. In fibrous membranes containing a chemically conjugated drug or agent, the drug or agent is primarily released into a medium by diffusion.

A working example of incorporation of gallium nitrate into fibrous membrane within the scope of the invention follows:

Approximately 1.5 g of the poly(ester amide) (8P4) was dissolved in 4 g of chloroform ($CHCl_3$ 99.8% HPLC grade), purchased from Aldrich Chemical Co., Inc. Gallium (III) nitrate hydrate, purchased from Sigma-Aldrich Inc. was dissolved in 500 mg 99.8% anhydrous N,N-dimethylformamide (DMF) (Aldrich), in amounts of 10 and 500 mg. The DMF-dissolved gallium nitrate was slowly added (droplet by droplet) to chloroform dissolved PEA without any visible precipitation, to provide 1.2, 1.0 and 0.2 grams per gram of poly(ester amide).

The homogeneous mixed drug (gallium nitrate)/polymer solution was electrospun at 15 kV under a steady flow rate of 0.025 mL/min using a spinneret with an orifice of diameter 0.2 mm as the jet with the distances of approximately 15-cm from the collecting plate. The electrospun fibers were collected in the form of thin fabric on a metal sheet (10 cm×15 cm) wrapped with wax paper. The fibrous fabric is peeled off the collecting wax paper.

In order to determine release profiles of gallium nitrate from the fabric, a calibration curve was prepared as follows: Solutions of known concentrations of gallium nitrate in chloroform (not completely dissolved) were extracted with 10-mL deionized water. The electrical resistance of the aqueous solutions from extraction was measured. A calibration curve was constructed based on conductivity (inverse of measured resistance) and known concentration of gallium nitrate.

Drug release was established at 1, 2, 3, 4, 5, 8, 12, 18 and 28 days by extraction with water and measuring conductivity and generating gallium nitrate release profiles for 1.2 grams of gallium nitrate per gram (8P4), 1.0 gram of gallium nitrate per gram (8P4) and 0.2 am of gallium nitrate per gram (8P4). In each case there was a burst of drug release within the first 5 days. The drug release profile suggests that release time is independent of the concentration of gallium nitrate incorporation in the fiber.

The role of gallium nitrate in promoting wound healing is demonstrated by Staiano-Coico, L., J. Surgical Res. 103, 134-140 (2002).

Example 1

2 g PEA was dissolved into 5.6 g chloroform, and in another bottle the gallium nitrate at the concentration of 8 mg, 80 mg, and 800 mg were dissolved into 1.2 ml DMF. The DMF was added to the PEA solution and electrospun onto wax paper at the conditions of 13 kV, a flow rate of 0.02 ml/min, and collection distance of 15 cm. A fibrous membrane containing PEA and gallium nitrate was obtained.

Example 2

2 g PEA (8-phe-4) was dissolved in 5.2~6.4 g dichloromethane (DCM), stirred 2-3 h to form a clear homogenous PEA/DCM solution. In another bottle, the gallium nitrate at the weight of 8 mg, 80 mg, and 800 mg were dissolved into 1.0~1.5 g DMF. The gallium nitrate/DMF solution was mixed with the PEA/DCM solution, and stirred for an additional 20 min.

The final solution was loaded in a 5 ml syringe with 0.6 mm inside diameter needle. Electrospinning was performed at 20 kV high voltage, 0.03 ml/min flow rate. The distance between the collector and needle is about 15 cm. Electrospinning continued for 2-3 hours until the electrospun mat got the needed thickness. The following fibrous membranes were obtained:

| Gallium nitrate loaded PEA electrospun samples | Theoretical Weight percent of gallium nitrate in the electrospun PEA material(%) |
|---|---|
| PEA-GN Low (8 mgGN in 2 g PEA) | 0.4% |
| PEA-GN Medium (80 mgGN in 2 g PEA) | 3.8% |
| PEA-GN High (800 mgGN in 2 g PEA) | 28.6% |

A PEA control membrane was produced in accordance with the PEA-GN fibrous membranes but with the exception that gallium nitrate was not incorporated into the PEA control fibrous membrane. The three PEA-GN electrospun samples and PEA control fibrous membrane were tested in Domestic Yorkshire pigs.

On the dorsum of Domestic Yorkshire pigs, a series of 1×2" partial thickness wounds were surgically created with a Dermatome (0.015 in). The PEA control and PEA-GN membranes were each placed over a wound as a dressing material. Dressing materials were tested in each possible location of the wound to minimize the possibility of wound location as a confounding variable. Wounds were photographed & assessed visually within the first 72 hours, and then twice weekly. Dressings were changed at each assessment until complete wound closure was achieved.

Wounds were biopsied for blinded histologic analysis on post-operative days (POD) 9, 16, 27.

Specimens were analyzed for reepithelialization, epidermal maturation, inflammatory infiltrate, dermal matrix remodeling, fibroplasia, and retention of foreign material. Immunohistochemical analysis was performed on the biopsy specimens using antisera for Von Willebrand Factor (VWE), Ki67 antigen, and TUNEL.

Wound closure: Each of the PEA-GN sites achieved complete wound closure after POD 2, whereas the control sites had not achieved complete wound closure and required re-dressing of test material. All wounds were closed after POD6.

Repithelialization: On routine H&E staining, PEA-GN sites peaked in number of keratinocyte layers at an earlier timepoint than PEA control. Yet, staining for Ki67, a marker for cell proliferation, demonstrated a blunting of proliferation in the GN-treated sites. The hypothesized mechanism of increased re-epithelialization is due to increased migration. The re-epithelialization observed in the PEA-GN sites does not appear to be due to an increase in cell proliferation. The proliferating cells that took up the Ki67 stain correspond to the basal stem cell layer.

Rete Ridge Formation: PEA control lagged behind PEA-GN in rete ridge formation. PEA-GN Low and PEA-GN High sites demonstrated rete ridge formation by POD9, whereas Control did not show signs of rete ridges until POD27. Since rete ridge formation is a requisite part of normal cutaneous repair post-injury, and its presence is a hallmark indicator of the skin's durability and resistance to sloughing and blistering, the earlier appearance of rete ridges in the ON-treated sites is a favorable finding.

Hyperkeratosis: At the first biopsy timepoint (POD9), a degree of parakeratotic hyperkeratosis was present in all sites, but was most prominent in PEA-GN Low, followed by PEA-GN High. On POD9, PEA control had mostly basket-weave type orthokeratosis A degree of parakeratotic hyperkeratosis was also present in all conditions at the second biopsy timepoint (POD16), but again was most prominent in PEA-GN Low. By POD16, however, PEA-GN High and PEA control had an approximately equal mixture of parakeratotic and basket-weave type orthokeratosis. By the last biopsy timepoint all conditions exhibited similar keratin production of an orthokeratotic, basketweave type, with thicker, denser deposits overlying regions of increased epidermal thickness.

Fibroplasia/Fibrosis: PEA control demonstrated the greatest percent fibrosis and dermal cell proliferation at the latest timepoint (POD27). At POD9 all 3 conditions had a linear band of superficial dermal edema and early fibroplasia, but was most pronounced in PEA-GN Low, followed by PEA control. The decline observed between POD9 and POD16 in percent edema and fibroplasia in the PEA-GN Low and PEA control conditions is most likely due to resolution of edema; Ki67 staining showed a positive dermal cell proliferation trend between POD9 and POD16 for these conditions. On POD27 a linear band of organizing fibrosis was present in the superficial dermis in all three sites, and was variable in thickness in different areas. The thickest foci of fibrosis tended to correspond with regions of neovascularity. In both average and maximum fibrosis PEA control was thickest, followed by PEA-GN Low and then PEA-GN High.

While all of the PEA-GN membranes enhanced healing, PEA-GN Low showed signs of most exuberant healing at earlier timepoints. Of all conditions on POD9, PEA-GN Low had the thickest epidermis, the most parakeratotic hyperkeratosis, and the most pronounced rete ridge formation. The PEA Control, on the other hand, demonstrated a more protracted healing response. The control condition did not display any parakeratotic hyperkeratosis until POD16, and did not demonstrate it's peak number of keratinocyte layers, or rete ridge formation, until POD27. In addition, whereas PEA-GN Low demonstrated more edema and fibroplasia than the PEA control at earlier timepoints, the PEA control displayed the most fibrosis and dermal proliferation by POD27. At no time did any of the sites demonstrate sign of infection, retention of foreign material, or any adverse reactions. There was no significant difference detected between conditions in degree of inflammatory infiltrate. Von Willibrand staining and TUNEL staining did not yield any significant findings.

Example 3

A poly(ester amide) ($M_n$=1.36×10$^4$ g/mol) used in this example was synthesized by solution polycondensation of di-p-nitrophenyl sebacate and p-toluenesulfonic acid salt of L-phenylalanine butane-1,4-diester, and was labeled as 8-Phe-4, where 8 and 4 indicated the number of methylene groups between two adjacent amide and ester linkages, respectively (See R. Katsarava, V. Beridze, N. Arabuli, D. Kharadze, C. C. Chu, and C. Y. Won, *J Polym Sci A: Polym. Chem.* 37, 391 (1999)).

4-amino-TEMPO nitroxyl radical stock solution was prepared in DMF (4-amino-TEMPO/DMF) at a concentration of 15 mg/mL and stored in a refrigerator at ~2° C. before use. 8-Phe-4 was dissolved in chloroform at room temperature by gently stirring for 2 to 3 hrs, and then mixed with 4-amino-TEMPO/DMF solution to achieve 8-Phe-4 concentrations ranging from 43% wt/vol to 14% wt/vol, and to reflect a 4-amino-TEMPO to 8-Phe-4 feed ratio of 10.0 mg to 1 g. The volume ratio of chloroform to DMF in the mixed solvent was controlled at the level of 2 to 1. To prepare a 43% wt/vol PEA electrospinning dope solution, 1.5 g of 8-Phe-4 was dissolved in 2.29 mL of chloroform first, and then mixed with 1 mL 4-amino-TEMPO stock solution (15 mg 4-amino-TEMPO/mL DMF) and 0.1450 mL of additional pure DMF.

Electrospinning was performed using a 5 mL glass syringe attached to a 26 gauge needle (Hamilton 90026, VWR Inc.), which was connected to a high voltage power supply (Gamma High Voltage Supply, ES 30-0.1P). The 8-Phe-4 concentration was varied from 14 to 43% in three types of solvents: chloroform, DMF, and a mixed solvent of chloroform and DMF at three volume ratios of chloroform to DMF (100/0, 66.7/33.3, and 0/100). The electrospinning dope solutions were then fed to a syringe and injected at a rate of 0.02 mL/min using a syringe pump (Model 200 KdScientific). The tip-to-collector distance and electrospinning voltage was about 15 cm and 14 kV, respectively. A piece of wax paper was taped on the top of a piece of grounded aluminum foil and used as the collector.

For the purposes of comparison, 8-Phe-4 films were cast from ~7% 8-Phe-4 solution in chloroform in glass petri dishes at a room temperature. After chloroform was completely evaporated, the films were further dried in a vacuum oven for at least 24 hrs at room temperature. The film thickness was about 0.20 to 0.30 mm.

The morphology of the electrospun 8-Phe-4 fibers was observed with a scanning electron microscope (SEM, LEICA 440). The fibers were coated with gold and observed under 25 kV accelerating voltage. The diameters of about 100 electrospun fibers were measured by an image analysis software (Scion Image, NIH Image software) to obtain fiber size distribution. The thermal behavior of 8-Phe-4 electrospun fibers was determined with a differential scanning calorimeter (DSC) (DSC 2920, TA Instruments Inc., New Castle, Del.) using ~5.0 mg samples at a 10° C./min heating rate in nitrogen at a gas flow rate of 25 mL/min. The DSC data were compiled and analyzed by the software associated with the DSC instrument. The glass transition temperature ($T_g$) was recorded, and the melting point was determined at the onset of the melting endotherm. The molecular weight of 8-Phe-4 was determined by a gel permeation chromatograph (GPC, Waters Associate, Inc., Milford, United States) equipped with a high-pressure liquid chromatography pump, a Waters 486 UV detector, and a Waters 2410 differential refractive-index detector. Tetrahydrofuran (THF) was used as the eluent (1.0 mL/min). The columns were calibrated with polystyrene standards with a narrow MWD.

The in vitro degradation of 8-Phe-4 electrospun fibers were assessed by changes in fiber morphology, weight loss and molecular weight. Fibrous membranes with a thickness of 0.251±0.02 mm were cut into 2×2 cm pieces (~50 mg each).

Three pieces of fibrous membranes were placed in a capped glass vial filled with 10 mL of PBS buffer (pH=7.42) with or without enzymes and removed at predetermined period, followed by rinsing with distilled water and vacuum dry at room temperature until a constant weight was achieved. The weight loss was determined by the follow equation:

$$\text{Weight loss} = (Wi - Wt)/Wi \times 100\%$$

where Wi is the initial dry weight of the fibrous mat at time 0 and Wt is the dry weight of the sample at the specific degradation time. In the case of enzymatic biodegradation, 8-Phe-4 electrospun fibrous membranes were immersed in 10 mL PBS solution having 0.1 mg/mL α-chymotrypsin, and the enzyme solution was refreshed every 24 hrs. All the biodegradation tests were done in a water bath shaker (100 cycles/min) at 37° C.

The in vitro release of 4-amino-TEMPO nitroxyl radicals from electrospun PEA fibers was investigated by immersing ~300 mg 8-Phe-4 electrospun nano fibrous mat into a glass vial filled with 5 mL of 0.1M phosphate buffer solution of pH=7.42. The 8-Phe-4 nano fibrous mat was pre-loaded with 4-amino-TEMPO at a 10.0 mg 4-amino-TEMPO per g 8-Phe-4 and electrospun from a 39% wt/vol 8-Phe-4 solution in the mixture solvent of chloroform and DMF at volume ratio of 2 to 1. The glass vial was then placed in a water bath shaker maintained at 37° C. and 100 cycles/min. 10 μl of supernant of the vial was taken at a determined time and the amount of 4-amino-TEMPO nitroxyl radicals was measured by electron spin resonance (ESR) as a function of incubation time.

Three samples were taken for each measurement and the average results were reported. The ESR spectra at X-band were obtained from a Bruker 200D SRC spectrometer operating at 9.6 GHz, using 100 KHz modulation. The ESR signal intensity which is proportional to the mass of 4-amino-TEMPO nitroxyl free radical was obtained by a double integration of the recorded first derivative signals. A linear correlation ($\gamma^2=0.9996$) between the ESR signal intensity and the mass of nitroxyl radical ranging from 1.67 μg to 0.05 μg was obtained. The actual amount of 4-amino-TEMPO nitroxyl radicals loaded into the electrospun fibers was also determined by a complete dissolution of 8-Phe-4/4-amino-TEMPO electrospun fibrous membranes in DMF and the actual pre-loaded 4-amino-TEMPO amount within 8-Phe-4 fibers was calculated from the established calibration curve. The nitroxyl radicals released was measured in triplicates and expressed in the percentage of the initial pre-loaded amounts in the 8-Phe-4 fibers.

8-Phe-4 can be readily dissolved in chloroform and DMF in up to 55% and 64% (wt/vol) concentrations, respectively. While fibers were obtained from electrospinning of 8-Phe-4 in a DMF solution, these fibers did not perform as well under the experimental conditions. 8-Phe-4 fibers seemed more likely to fuse together and in some locations formed a continuous thin-film appearance. As a result, 8-Phe-4 fibers produced with DMF were not always dry when reaching the collecting plate, i.e., wet fibers aggregating together to form film-like appearance.

The addition of chloroform, which has a much lower boiling point (~62° C.) than DMF, produced drier fibers. Distinctive 8-Phe-4 fibers of average diameter 3.5 μm were obtained by electrospinning 32% 8-Phe-4 in chloroform. However, due to the very fast evaporation of chloroform from the 8-Phe-4 solution jets during electrospinning, the jets were sometimes prone to solidification and could not be fully stretched or drawn in an electric field to form submicron fibers. In this regard, the syringe was also prone to being blocked by solidified 8-Phe-4 and needed to be cleaned periodically to maintain the electrospinning. This resulted in a low fiber collection efficiency.

Figure 1B:
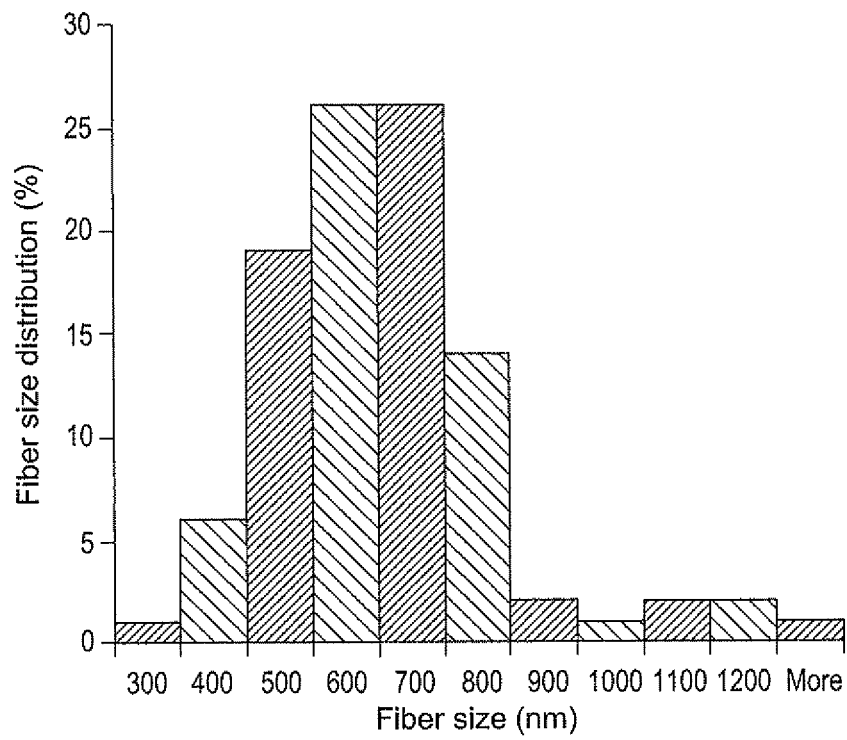

When a mixture of DMF and chloroform was used as the solvent for 8-Phe-4 electrospinning, the resulting 8-Phe-4 fibers showed smaller fiber diameters than those from chloroform alone but also could be collected continuously for several hours without cleaning. A solution for electrospinning that provided particularly good results was found to be 39% wt/vol 8-Phe-4 dissolved in the chloroform/DMF solvent mixture of 2 to 1 vol ratio, and the average 8-Phe-4 fiber diameter obtained under this electrospinning condition was about 640 nm. FIG. 1 shows a fiber size distribution of 8-Phe-4 fibers electrospun from (a) chloroform (32%) and (b) a mixture of chloroform and DMF at a volume ratio of 2:1 (39%).

DMF may slow down the solvent evaporation and allows the 8-Phe-4 solution jets to be fully extended by the electrostatic force to achieve smaller fiber diameters. In addition, DMF has a higher dielectric constant (~38.2) than chloroform (~4.8), which may increase the electrostatic force exerted on the 8-Phe-4 solution jets during electrospinning, and thus may result in smaller fiber sizes. The incorporation of 4-amino-TEMPO at the concentration of 10.0 mg/g 8-Phe-4 in the mixture of chloroform and DMF did not affect the fibers size or morphology. FIG. 1 shows fiber size distribution of 8-Phe-4 fibers electrospun from (a) chloroform (32%) and (b) a mixture chloroform and DMF at a volume ratio of 2:1 (39%). The values in parentheses are the concentration (w/v) of 8-Phe-4 in the corresponding solvents.

Although electrospun 8-Phe-4 fibers were randomly distributed, some unusual distribution patterns, such as radiation and parallel orientation, were observed for 8-Phe-4 fibers (See Chu et al, Nitroxyl Radical Incorporated Electrospun Biodegradable Poly(ester Amide) Nanofiber Membranes, *Journal of Biomaterials Science* 20 (2009) 341-361).

Figure 2:
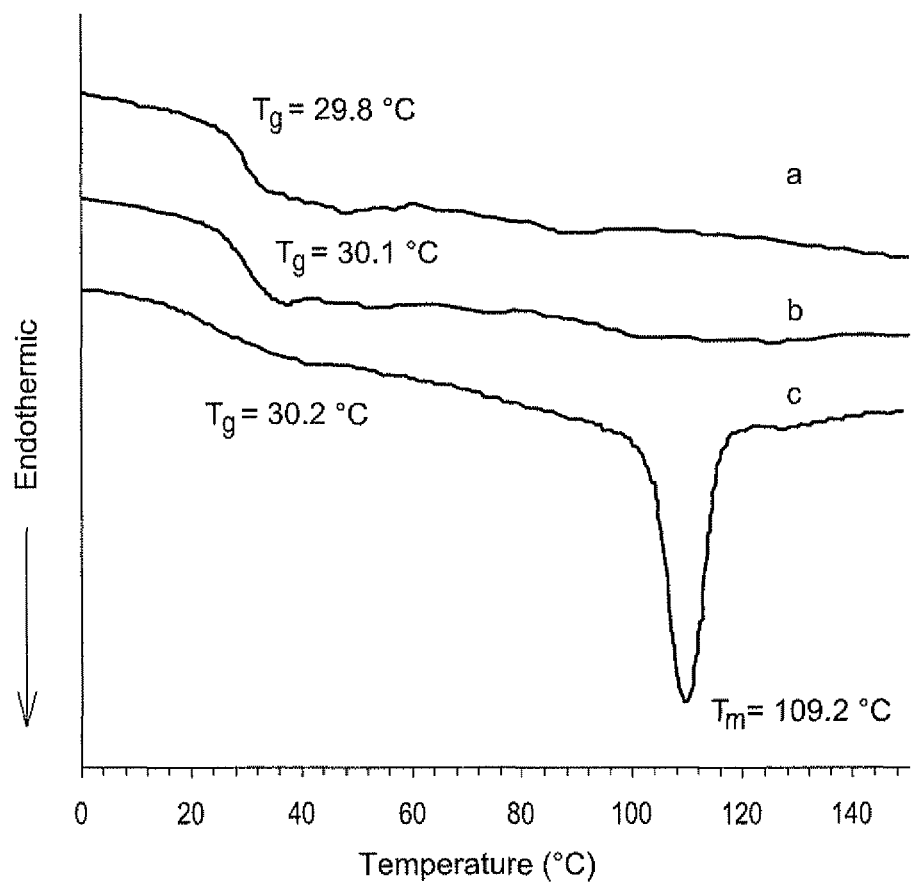
FIG. 2 shows a DSC thermogram.

The thermal behaviors of 8-Phe-4 electrospun fibers of different fiber sizes were investigated by DSC and compared with 8-Phe-4 solvent-cast film. The DSC thermograms were shown in FIG. 2. A significant melting peak at 109.2° C. was observed for the 8-Phe-4 solvent-cast film but not the electrospun fibers (FIG. 2*a*, and 2*b*). When 8-Phe-4 film was cast from a chloroform solution, 8-Phe-4 molecules had enough time to rearrange themselves to crystallize. However, during electrospinning, the solvent was removed from solution jet too quickly for 8-Phe-4 macromolecules to rearrange for crystallization, i.e., forming amorphous 8-Phe-4 fibers.

Figure 3:
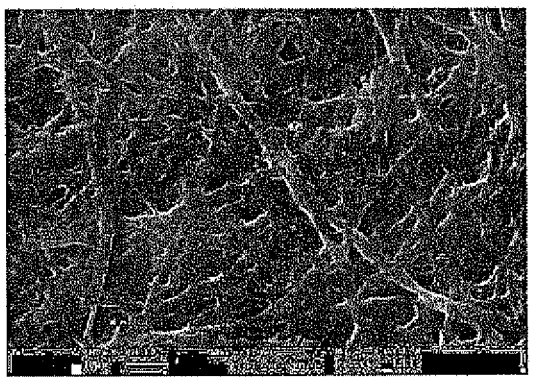
FIG. 3 is an SEM images of 640 nm 8-Phe-4 electrospun fibers after incubation in PBS buffer at 37~C after 1 day.

Both 8-Phe-4 electrospun fibers and cast films showed virtually the same $T_g$ around 30° C., e.g. 29.8° C. (640 nm 8-Phe-4 fibers), 30.1° C. (3.5 μm 8-Phe-4 fibers), and 30.2° C. (solvent-cast film). The thermal data in FIG. 3 also shows that 8-Phe-4 electrospun fibers exhibited a much larger heat capacity change than the cast film in the glass transition region.

The biodegradation profiles of 8-Phe-4 electrospun fibrous membranes were investigated in PBS buffers with and without enzymes. 8-Phe-4 electrospun fibrous membranes shrank dramatically after being immersed in PBS buffer at 37° C. for a few hours and no her shrinkage was observed thereafter. The low glass transition temperature (<37° C. incubation temperature) and amorphous nature of 8-Phe-4 electrospun fibers caused 8-Phe-4 molecular chains to relax very quickly and thus the shrinkage occurred during the first few hours of incubation. The relaxation of 8-Phe-4 macromolecules also resulted in a great changes in the morphology of 8-Phe-4 electrospun fibers during the biodegradation process.

Figure 4:
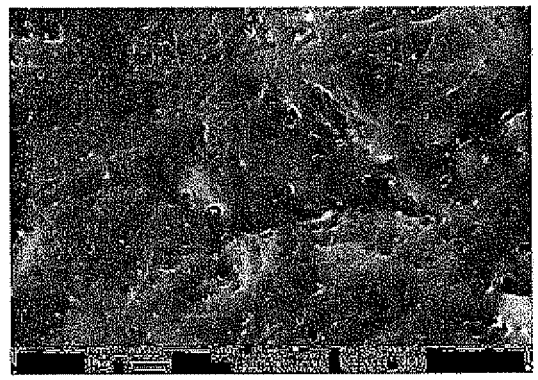
FIG. 4 is an SEM images of a 640 nm 8-Phe-4 electrospun fibers after incubation in PBS buffer at 37~C after 7 days.
Figure 5:
FIG. 5 is an SEM images of a 640 nm 8-Phe-4 electrospun fibers after incubation in PBS buffer at 37~C after 14 days.
Figure 6:
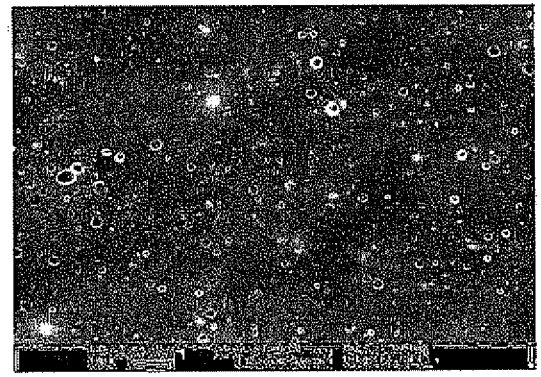
FIG. 6 is an SEM image of a 640 nm 8-Phe-4 electrospun fibers after incubation in PBS buffer at 37~C after 30 days.
Figure 7:
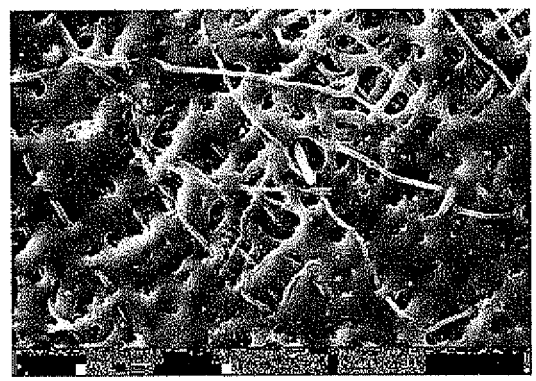
FIG. 7 is an SEM image of a 3.5 μm 8-Phe-4 fiber after incubation for 30 days.

Although 8-Phe-4 electrospun fibers showed the same glass transition temperature around 30° C. regardless of fiber sizes, smaller fibers appeared to loose their structure integrity more easily. The 640 nm diameter 8-Phe-4 electrospun fibers started to fuse together and lost fibrous appearance within one day of incubation in PBS buffer (FIG. 3), and fibrous appearance was hardly visible after one week (FIG. 4), and was completely lost after two weeks of incubation (FIG. 5). At the end of 4 weeks, the fibrous membranes became transparent porous films (FIG. 6). However, larger diameter (3.5 μm) 8-Phe-4 fibrous membranes still kept some fibrous appearance even after one month degradation in PBS buffer (FIG. 7).

Although 640 nm diameter 8-Phe-4 electrospun fibers were amorphous and did not show a melting peak, the incubated samples exhibited a strong melting peak at the same temperature as 8-Phe-4 bulk material. In the meantime, the heat of fusion increased from 15.7 J/g for 1 day incubated 8-Phe-4 fibers to 17.1 J/g for 1 month incubated same fibrous sample, suggesting an increase in the degree of crystallinity with increasing incubation time. Because of the strong intermolecular hydrogen bond in 8-Phe-4, the PBS incubation medium could reduce these intermolecular forces, particularly at an incubation temperature above its $T_g$; such destruction of intermolecular forces would facilitate 8-Phe-4 macromolecule mobility and reorganization toward crystallization.

An increase in glass transition temperature ($T_g$) of the 640 nm diameter 8-Phe-4 electrospun fibers was also observed with increasing incubation time. For example, a significant increase in $T_g$ (31%) was observed with only 1 day incubation (from 29.8° C. at 0 day to 38.9° C. at 1 day), and $T_g$ increased her to 41.0° C. at the end of one month incubation.

This increase in $T_g$ with incubation time was believed to be attributed to the formation of crystalline structure upon incubation as evident in the appearance of melting peaks at 1 and 30 days incubation. The formation of crystalline structure could restrict the segmental chain motion in the amorphous domain, i.e., higher $T_g$. Once the crystalline structure formed during the first day of incubation and the glass transition temperature became greater than the incubation temperature, the mobility of 8-Phe-4 macromolecules was restricted at the incubation temperature (37° C.), and thus a further increase in glass transition temperature with increasing incubation time became smaller.

The size of the 8-Phe-4 fibers was also found to affect the magnitude of $T_g$ increase with incubation time. The increase in $T_g$ upon incubation was more significant for smaller fibers. For example, after one month incubation in PBS buffer at 37° C., the $T_g$ of 640 nm 8-Phe-4 electrospun fibers increased 11.2° C. (38% increase from 29.8° C. to 41° C.), but the 3.5 μm 8-Phe-4 electrospun fibers had only 7.4° C. increase (25% increase from 30.1° C. to 37.5° C.). The solvent-cast 8-Phe-4 film had the smallest increase in $T_g$, 3.4° C. (11% increase from 30.2° C. to 33.6° C.). The reason for the largest increase in $T_g$ in the smallest size 8-Phe-4 fibers upon degradation may be attributed to their extraordinary surface area to volume ratio that led to more significant change of $T_g$ than the solvent-cast film. In addition, the electrospun PEA fibers were totally amorphous, while the solvent-cast film was semi-crystalline before degradation; and it is known that an initially totally amorphous structure could permit a larger $T_g$ change upon degradation.

Due to the initial semi-crystalline structure in the solvent-cast 8-Phe-4 film, the heat of fusion for the 8-Phe-4 film after 1 month of incubation was also much higher, 21.9 J/g, when compared with 16.8 and 17.1 J/g for the 3.5 μm and 640 nm electrospun fibers, respectively.

Both 8-Phe-4 electrospun fibrous membranes and solvent-cast films showed slight weight loss and molecular weight reduction during one month degradation in PBS buffer at 37° C. The weight loss was about 1.2% and 4.0% for the 640 nm 8-Phe-4 fibers and solvent-cast 8-Phe-4 film, respectively. The molecular weight reduction was about 11.7% for the fibers and 8.1% for the films.

Figure 8:
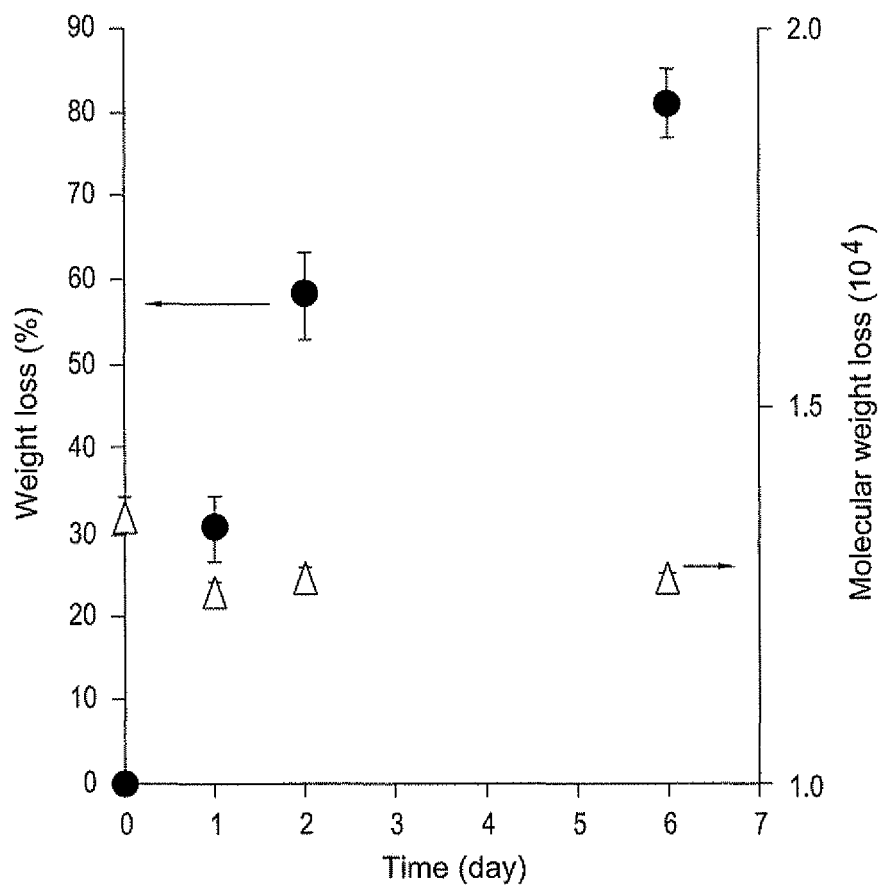
FIG. 8 shows the weight loss (●) and molecular weight reduction (Δ) of 640 nm electrospun fibers incubated in 0.1 mg/ml α-chymotrypsin/PBS solution at 37~C.

The effect of α-chymotrypsin enzyme (0.1 mg/mL PBS) on the degradation of PEA nano fibers was also investigated at 37° C. The data on weight loss and molecular weight reduction of PEA fibers are shown in FIG. 8. α-chymotrypsin is a protease enzyme which can hydrolyze ester linkages at the C-terminal of hydrophobic α-amino acids like L-phenylalanine. The 640 nm 8-Phe-4 electrospun fibers showed about 60% weight loss within 2 days of biodegradation and reached more than 80% weight loss after 6 days. During the same degradation period, almost no molecular weight reduction of the 8-Phe-4 fibers was detected (FIG. 8). This biodegradation data suggested that the enzymatic biodegradation of 8-Phe-4 electrospun fibers proceeded in a surface erosion mechanism rather than bulk degradation as aliphatic polyesters polylactide, polyglycolide and their copolymers) do.

Figure 9:
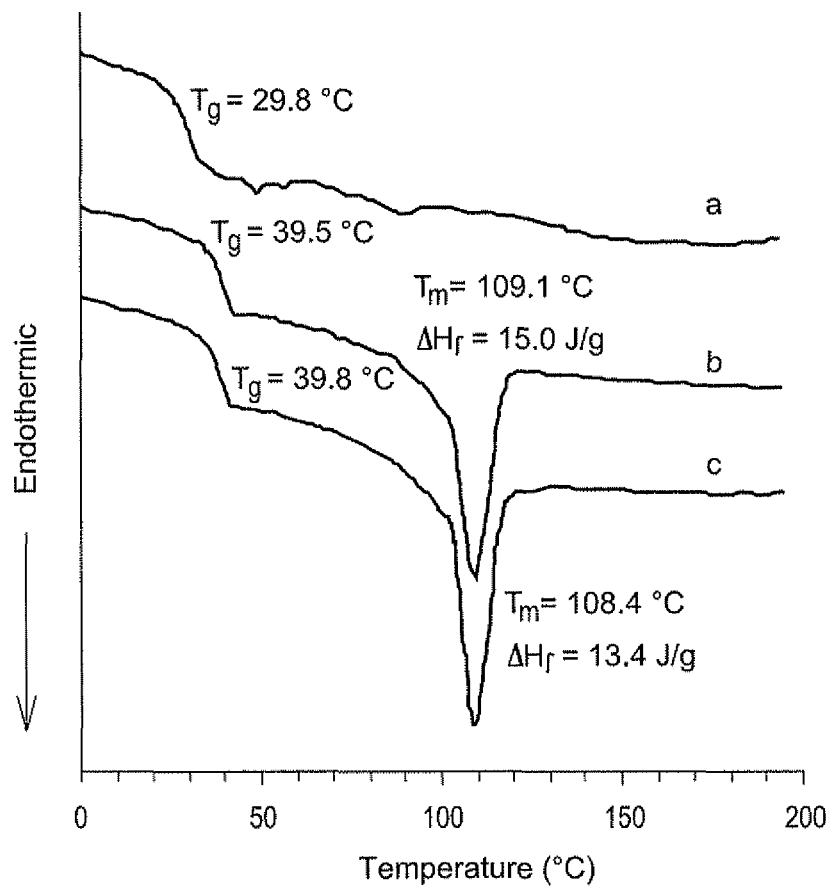
FIG. 9 is a DSC thermogram of (a) electrospun 640 nm is (b) after 1 day and (c) 6 days of degradation at 37~C in 0.1 mg/ml α-chymotrypsin/PBS solution.

During the enzymatic biodegradation, 8-Phe-4 electrospun fibers also showed a drastic increase in their glass transition temperature, most significantly in the first day of biodegradation. As shown by the DSC thermograms in FIG. 9, the glass transition temperature increased from 29.8° C. for the original non-biodegraded fibers (FIG. 9a) to 39.5° C. and 39.8° C. for the 1 (FIG. 9b) and 6 days (FIG. 9c) biodegraded fibers, respectively. A melting peak (109.1° C.) and a heat of fusion of 15.0 J/g were observed for the 1 day enzymatic biodegraded 8-Phe-4 electrospun fibers (FIG. 9b). Instead of the observed increasing heat of fusion with incubation time in a PBS buffer case, the heat of fusion and melting point of 8-Phe-4 electrospun fibers decreased to 13.4 J/g and 108.4° C., respectively, after 6 days of enzymatic biodegradation, an indication that not only the amorphous region but also the crystalline structure of the 8-Phe-4 electrospun fibers had begun to degrade due to α-chymotrypsin.

4-amino-TEMPO was physically pre-loaded into the 640 nm 8-Phe-4 electrospun fibers at a loading level of 10.0 mg TEMPO per gram of 8-Phe-4. Since 4-amino-TEMPO is a free radical, the actual amounts of 4-amino-TEMPO loaded into the 8-Phe-4 electrospun nanofibers and its subsequently release from the fibers in either PBS buffer or a α-chymotrypsin solution (0.1 mg/mL α-chymotrypsin) were quantified by ESR.

Figure 10A:
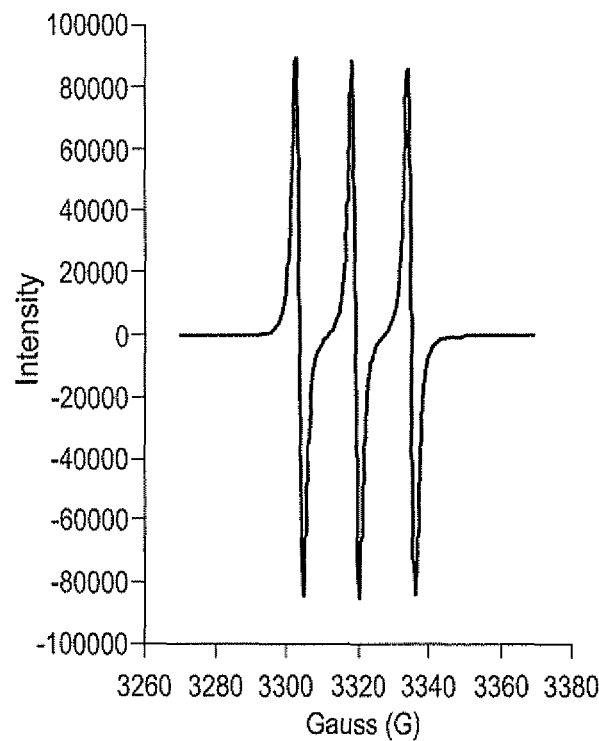
FIG. 10 is an ESR spectra of 4-amino-TEMPO in (a) DMF solution and (b) solid 640 nm electrospun fibers.
Figure 10B:
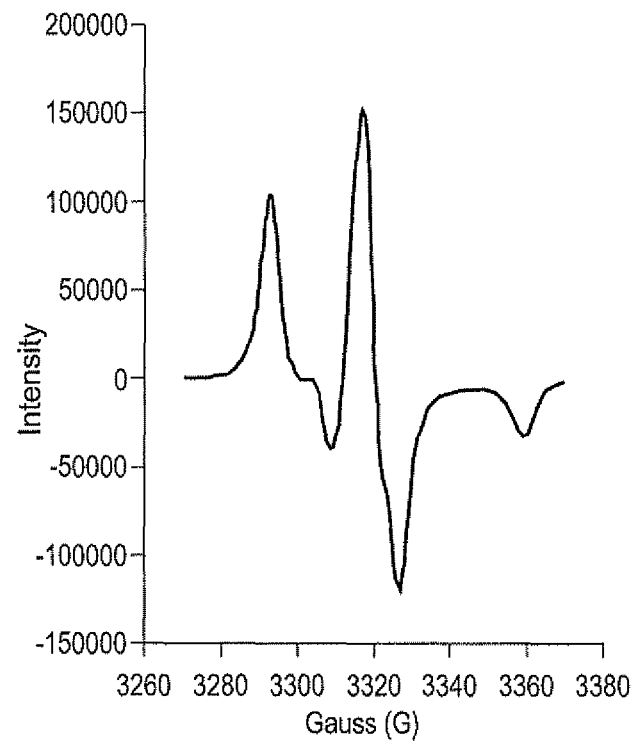

The ESR signal of free 4-amino-TEMPO nitroxyl radicals dissolved in DMF or PBS buffer at a low concentration (e.g., 0.2 mg/mL) shows the characteristic evenly split three spectral lines due to the spin quantum number of nitrogen being 1 (FIG. 10a). This symmetrical and well-defined ESR spectrum of free 4-amino-TEMPO, however, changed to a very diffused and broadened line width of varied intensity ESR spectrum after 4-amino-TEMPO was physically incorporated into 8-Phe-4 nanofibers (FIG. 10b). The ESR spectrum of the 4-amino-TEMPO impregnated 8-Phe-4 electrospun fibers (FIG. 10b) also suggests that the nitroxyl radicals were homogeneously dispersed within the 8-Phe-4 electrospun fibers at the molecular level. As expected, the 8-Phe-4 electrospun fibrous membranes without 4-amino-TEMPO did not show any ESR signals since 8-Phe-4 macromolecules do not have any free radical characteristic.

The actual loading level of 4-amino-TEMPO in the 8-Phe-4 nano fibers was quantified by dissolving the nitroxyl radical loaded 8-Phe-4 nanofibers in DMF first, and then comparing the measured ESR signal intensity with the preconstructed calibration curve. The results showed that about 97% of 4-amino-TEMPO in the electrospinning dope solution was actually loaded into 8-Phe-4 nanofibers. The ESR spectrum of the 4-amino-TEMPO recovered from the complete dissolution of 8-Phe-4 nanofibers also suggest that the characteristics of 4-amino-TEMPO nitroxyl free radicals were not affected by electrospinning process.

Figure 11A:
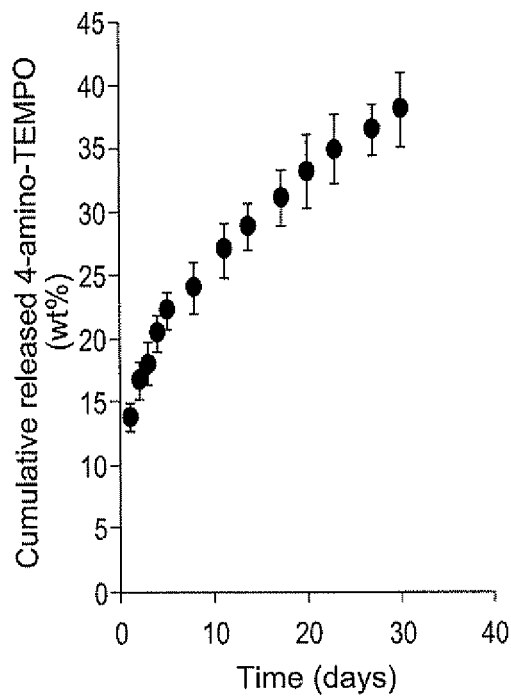
FIG. 11 shows the cumulative release of 4-amino-TEMPO from 640 nm electrospun fibers in a PBS medium at 37~C as a function of (a) time and (b) square root of time.
Figure 11B:
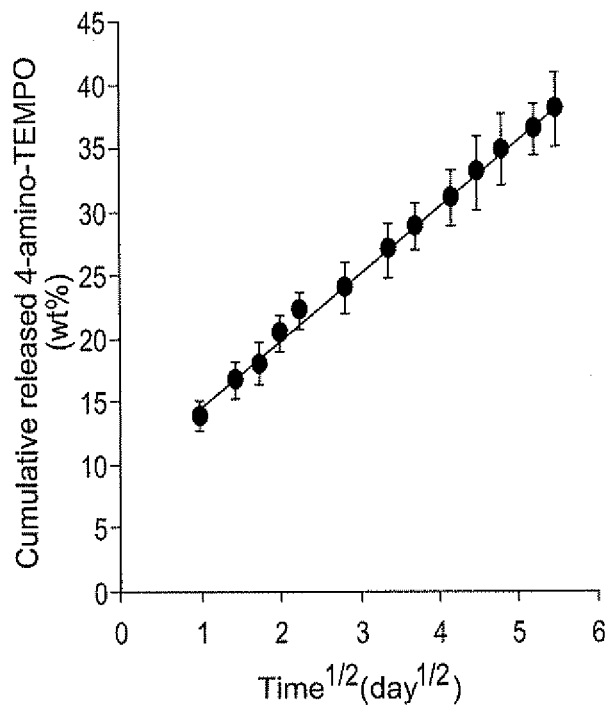
Figure 12:
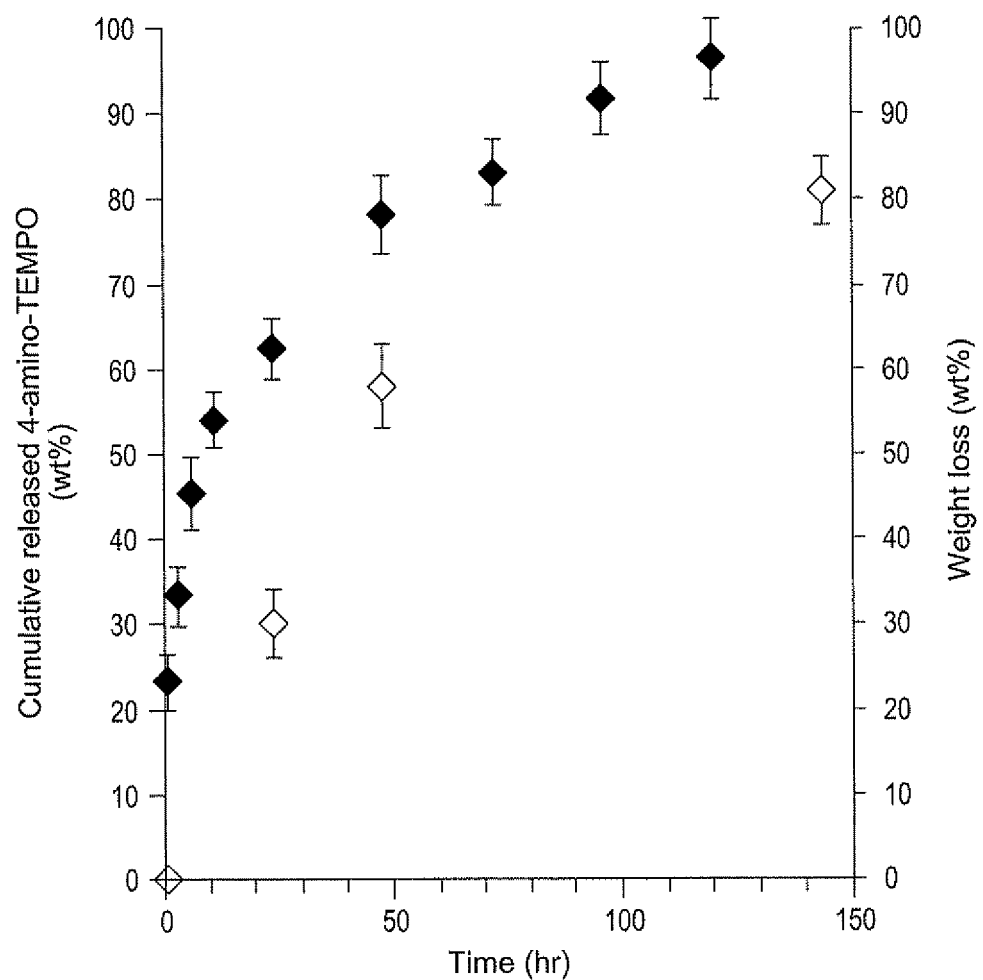
FIG. 12 shows the cumulative release of 4-amino-TEMPO (solid diamond shape) and the weight loss (lain diamond shape) of 640 nm electrospun fibrous matrix in 0.1 mg/ml α-chymotrypsin/PBS buffer solution at 37~C.

The cumulative release profiles of 4-amino-TEMPO from the 640 nm 8-Phe-4 nanofibers were investigated in a pH 7.42 PBS medium at 37° C. with and without α-chymotrypsin (FIGS. 11 and 12). In a PBS medium alone, an initial burst release, about 14% of the total loaded nitroxyl radical, was observed during the first day of incubation, which was followed by a steady release in an one month period with a total release of 38%. Due to the low drug loading amount (1% of 8-Phe-4 weight) and the gradual loss of the fiber morphology as well as the increasing degree of crystallinity of PEA electrospun fibers during the incubation, more than 60% of the 4-amino-TEMPO was still entrapped inside the 8-Phe-4 matrix under a PBS environment. This near 60% residual nitroxyl radical was further confirmed by measuring the ESR signal intensity of a completely dissolved one-month incubated 8-Phe-4 fibrous membrane in DMF, which was about 58% of the initial loading level. It was further verified that the recovered residual 4-amino-TEMPO retained its free radical characteristics as free 4-amino-TEMPO over the entire 1-month incubation in PBS medium at 37° C.

The release of 4-amino-TEMPO from 8-Phe-4 nanofibrous membranes in a α-chymotrypsin solution (0.1 mg/mL α-chymotrypsin) also showed a two-phase release pattern but with significantly faster and larger magnitude when compared with the release profile in a PBS buffer alone (FIG. 7 vs. 8). The slope of the initial linear part of the release profile was 72 (%/day) (FIG. 8), which was more than 35 times the value in a PBS medium alone, 2.0 (%/day) (FIG. 7). In a α-chymotrypsin solution, more than 23% and 50% of the incorporated TEMPO were released within the $1^{st}$ and 11 hrs, respectively. The TEMPO was completely released from the 8-Phe-4 nanofibers within 120 hours. Compared with the degradation profile of 8-Phe-4 electrospun fibers (weight loss data in FIG. 8), the TEMPO release proceeded at a much faster rate especially during the first 11 hrs of the enzymatic biodegradation, which indicated that the TEMPO was released by the synergetic effects of both diffusion and matrix erosion.

Thus, biodegradable 4-amino-TEMPO incorporated 8-Phe-4 electrospun nanofiber membranes were successfully fabricated by electrospinning method in a binary solvent of DMF and chloroform. The average fiber diameter was about 640 nm. Near 97% of 4-amino-TEMPO nitroxyl free radicals in 8-Phe-4 electrospinning solution was loaded into 8-Phe-4 nanofibers. About 38% of the loaded 4-amino-TEMPO was released in a pH 7.42 PBS medium during the 1-month incubation period at 37° C., and the release profile was controlled by the Fickian diffusion mechanism.

During the incubation in PBS buffer, 8-Phe-4 electrospun fibers gradually lost their fibrous structure and became a transparent film after 1 month with slight weight loss and molecular weight reduction. In an α-chymotrypsin solution (0.1 mg/mL α-chymotrypsin), 8-Phe-4 nano fibrous membranes biodegraded via a surface erosion mechanism with more than 80% weight loss within 6 days.

Due to the unexpected and synergetic effect of 8-Phe-4 biodegradation and drug diffusion of TEMPO, more than 50% of the loaded 4-amino-TEMPO was released within 11 hrs in the enzyme medium followed by a complete release within 120 hrs.

Example 4

I. Poly(ester amide) (8-phe-4) Electrospinning Method 2 g Polyesteramide (8-phe-4) is dissolved in 5.2~6.4 g dichloromethane (DCM), and stirred for approximately 2-3 hrs to form a clear homogenous solution. 1 g of dimethylformamide (DMF) is added in this PEA/DCM solution prior to electrospinning. This solution is labeled as Solution IA. The final solution is loaded in a 5 ml syringe attached with 0.6 mm inside diameter needle. Electrospinning is performed at 20 kV and 0.03 mL/min flow rate. The distance between the collector and needle is about 15 cm. Electrospinning is continued for 2-3 hours until the electrospun mat reaches its desirable thickness. In order to make a tubular electrospun fibrous membrane, a Teflon-coated metal rod driven by a micro motor is used as the collector. PEA fibrous membranes are obtained II. Polyesteramide (8-phe-4) with Chemically Conjugated TEMPO and Electrospinning Method A PEA copolymer of 8-Phe-4-25-COOH (4.00 g) is dissolved in 25 mL of chloroform at room temperature, and a molar equivalent of 1,1'-carbonyldiimidazole (0.32 g) is then added. After 1 hour, 0.35 g of TEMPO in 5 mL of chloroform is slowly added into the reaction mixture at room temperature. The reaction mixture is stirred for 12 hrs, the solvent is evaporated, and the polymer is precipitated into cold ethyl acetate to give PEA-TEMPO product. The PEA-TEMPO conjugated polymer is redissolved in chloroform and cast into a thin film. The film is thoroughly washed with water to remove excess agents produced during the reaction, and dried under reduced pressure at room temperature. A PEA-TEMPO compound is obtained (Mass ratio: PEA/TEMPO=8000/156). 2 g PEA-TEMPO compound is dissolved in 5.2~6.4 g dichloromethane (DCM). 1 g dimethylformamide (DMF) is added in to the solution before electrospinning. The solution is identified as IIA.

III. Polyesteramide (8-phe-4) with Impregnated TEMPO and Electrospinning Method

A polyesteramide 8-Phe-4 (4.00 g) and TEMPO are dissolved in 5.2~6.4 g dichloromethane (DCM). 1 g dimethylformamide (DMF) is added in to the solution before electrospinning. The solution is identified as IIIA.

IV. Polycaprolactone (PCL) Electrospinning Method 2 g PCL is dissolved in 20~26 g chloroform after stirring for 2 hr. Before electrospinning, 4 g DMF is added into the solution. This solution is labeled as Solution B. The electrospinning parameters for this Solution B are similar to I above (i.e., 20 kV voltage, 0.02~0.04 ml/min flow rate, and 15 cm collect distance). The same electrospinning method as discussed in I above is used to obtain fibrous membranes containing PCL only (PCL).

V. PEA/PCL Composite Electrospinning Method

Solution IA, IIA, and IIIA are both combined with solution B (from II) in a feed ratio of 50 to 50 by weight and fast speed stirring. PEA/PCL and PEA/PCL with conjugated TEMPO, and PEA/PCL with impregnated TEMPO composite electrospun fibrous membranes are obtained, respectively. The PEA/

PCL composite electrospun fibrous membranes are made from a mixture of 4.2 g Solution IA (1 g PEA) and 13 g Solution B (1 g PCL) with similar electrospinning parameters for I, II, or III as discussed above (i.e., 20 kV voltage, 0.02~0.04 ml/min flow rate, 15 cm collect distance). PEA/PCL composite electrospun fibrous membranes are also obtained with a feed ratio of 20 to 80 by weight of PEA to PCL and fast speed stirring. PEA/PCL composite electrospun membranes are made from a mixture of 8.2 g Solution IA (2 g PEA) and 8 g Solution B (0.5 g PCL). The composite electrospun membranes obtained are as follows:

TABLE 1

| Sample | Size (mm) | Amount | Weight (g) | TEMPO |
|---|---|---|---|---|
| PEA/PCL (50/50) electrospun tubes (i.e., without TEMPO) | Diameter: 7 Length: 90 | 2 | 0.60 0.70 | N/A |
| PEA/PCL (50/50) with conjugated TEMPO eletrospun tubes | Diameter: 7 Length: 90 | 2 | 0.48 0.57 | Mass ratio: PEA/TEMPO = 8000/156 |
| PEA/PCL (50/50) with impregnated TEMPO electrospun tubes | Diameter: 7 Length: 90 | 2 | 0.54 0.57 | Mass ratio: PEA/TEMPO = 8000/156 |
| PCL electrospun tubes | Diameter: 7 Length: 90 | 2 | 0.42 0.51 | N/A |

An immunohistochemistry analysis with endothelial cell markers and inflammatory cell markers for each of three membranes (i.e., PCL, PEA/PCL, and PEA/PCL with conjugated TEMPO) was completed to determine the level in which each membrane inhibits intimal hyperplasia. Intimal hyperplasia is the thickening of the Tunica intima of a blood vessel as a complication of a reconstruction procedure or endarterectomy. Intimal hyperplasia is the universal response of a vessel to injury and is an important factor in late bypass graft failure, particularly in vein and synthetic vascular grafts.

Immunoreactivity was detected with positive staining in brown and counter staining in purple. Image were taken of each membrane.

Figures 13A, 13B:
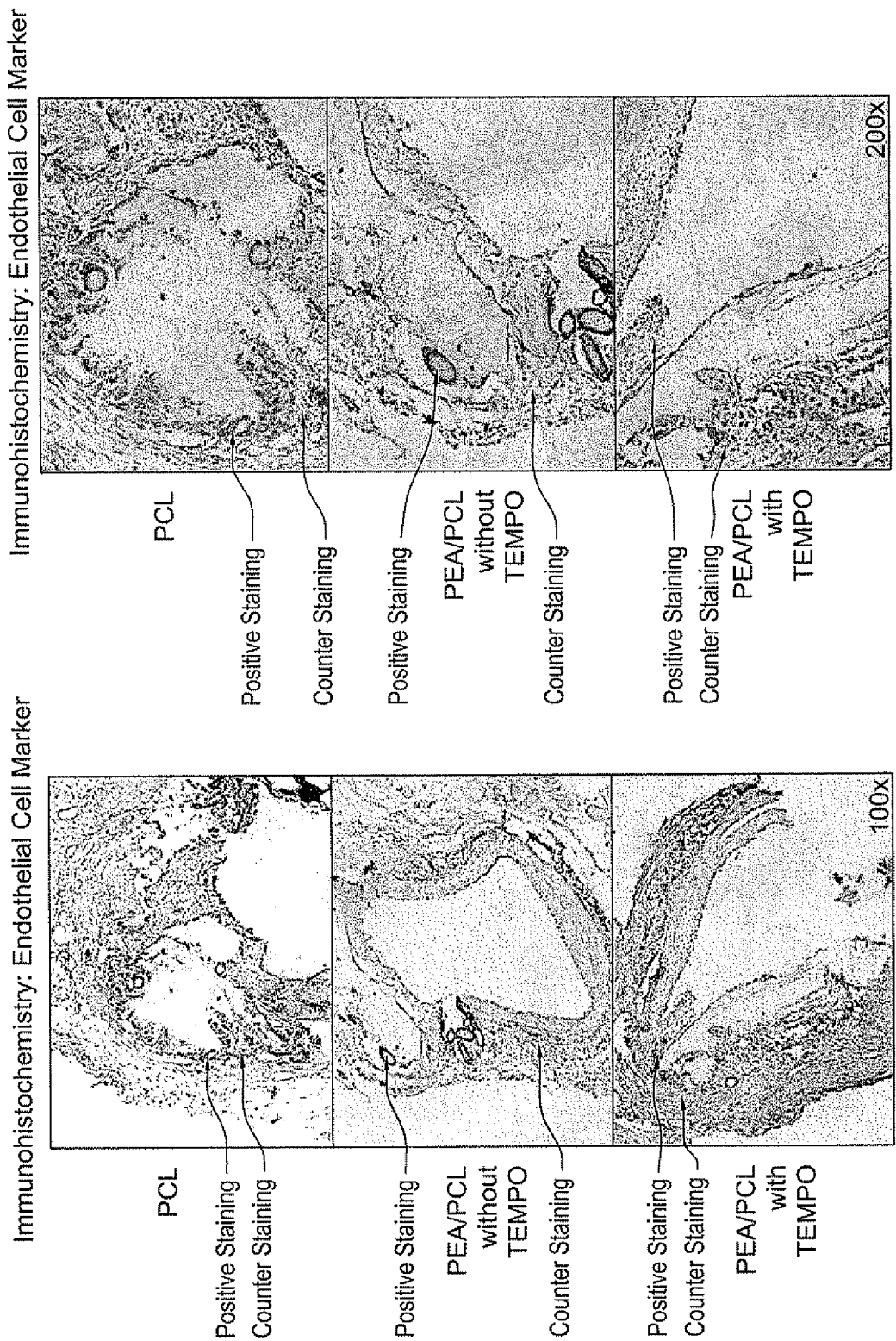
FIGS. 13(a) and (b) show the results of an immunohistochemistry analysis with endothelial cell markers at 100× and 200× magnification, respectively.

The results are shown in FIGS. 13 and 14. FIG. 13 shows the results of the immunohistochemistry analysis with endothelial cell markers at 100× and 200× magnification. FIG. 17 shows the results of the immunohistochemistry analysis with inflammatory cell markers at 100× and 200× magnification. Both FIGS. 16 and 17 label the results obtained with PEA/PCL with conjugated TEMPO as "PEA/PCL with TEMPO". The PEA/PCL with conjugated TEMPO inhibit intimal hyperplasia and the formation of endothelial cells on the lumen surface of the electrospun fibrous membranes.

In addition, immunostaining for monocyte/macrophage inflammatory cells show that PEA/PCL with TEMPO membranes in the rat aorta patch model were not obstructed with inflammatory cells adjacent to or within the membrane after 14 days. This is in contrast to the results obtained with the PCL and PEA/PCL membranes obtained after 14 days. A number of inflammatory cells were found adjacent to the PCL and PEA/PCL membranes after 14 days. Thus, the PEA/PCL with TEMPO membrane is non-inflammatory.

VARIATIONS

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A fibrous membrane comprising biodegradable electrospun poly(ester-amide) for use for biomedical application, wherein:

the fibrous membrane has an average fiber diameter ranging from 300 nm-1.2 μm, a median pore size ranging from 0.1 to 100 micrometer, a surface area ranging from 10 to 300 m²/g, and an average thickness ranging from 0.01 to 0.500 mm, and the fibrous membrane comprises a drug or agent, where the poly(ester-amide) has a reduced viscosity ranging from 1.0 to 2.0 dL/g and is selected from the group consisting of one or more subunits A, and one or more subunits B, and combinations thereof, where the one or more subunits A have the structure

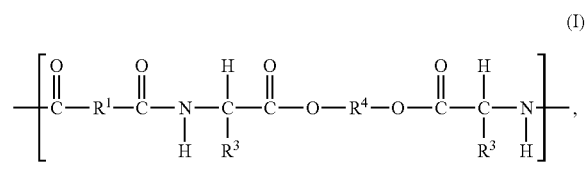

where $R^1$ is $(C_2\text{-}C_{20})$ alkylene, where $R^3$ is hydrogen, $(C_1\text{-}C_{20})$ alkyl, $(C_2\text{-}C_6)$ alkenyl, $(C_2\text{-}C_6)$ alkynyl or $(C_6\text{-}C_{10})$ aryl $(C_1\text{-}C_6)$ alkyl, and wherein $R^4$ is a $(C_2\text{-}C_{20})$ alkylene; and where the one or more subunits B have the structure

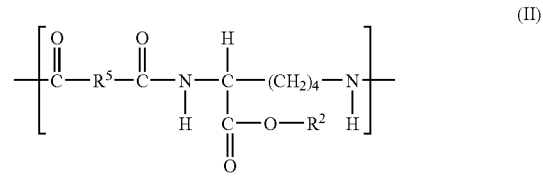

where $R^2$ is hydrogen or $(C_6\text{-}C_{10})$ aryl $(C_1\text{-}C_6)$ alkyl and where $R^5$ is $(C_2\text{-}C_{20})$ alkylene.

2. The fibrous membrane of claim 1 wherein, when the fibrous membrane is seeded with NHEK cells, the cells show cell attachment and proliferation in a Calcein-AM assay.

3. The fibrous membrane of claim 2 where the polyester amide has the structure (I) where $R^1$ is $(CH_2)_8$, $R^3$ is

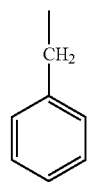

and $R^4$ is $C_4\text{-}C_8$ alkylene.

4. A method for making a fibrous membrane, wherein the fibrous membrane:

comprises biodegradable electrospun poly(ester-amide), has an average fiber diameter ranging from 300 nm-1.2 μm, a median pore size ranging from 0.1 to 100 micrometer, a surface area ranging from 10 to 300 m2/g, and an average thickness ranging from 0.01 to 0.500 mm, and comprises a drug or agent, the method comprising the steps of:
preparing an electrospinning solution of poly(ester-amide) by dissolving poly(ester-amide) in a mixture of chloroform and dimethylformamide (DMF);
solution electrospinning of the poly(ester-amide); and
varying thickness of the fibrous membrane and/or solution concentration and/or collection distance and/or voltage and/or fiber diameter to vary pore size.

5. The method claim 4, where the drug or agent is selected from the group consisting of 2,2,5,5-tetramethylpyrrolidine-1-oxy; 2,2,5,5-tetramethyl-3-pyrroline-1-oxy-3-carbonyl; 4-(N,N-dimethyl-N-hexadecyl)ammonium-2,2,6,6-tetramethylpiperidine-1-oxy, iodide (CAT16); 4-trimethylammonium-2,2,6,6-tetramethylpiperidine-1-oxy, iodide (CAT 1); 3-amino-2,2,5,5-tetramethylpyrrolidine-1-oxy; N-(3-(iodoacetyl)amino)-2,2,5,5-tetramethylpyrrolidine-1-oxy (PROXYL 1A); succinimidyl 2,2,5,5-tetramethyl-3-pyrroline-1-oxy-3-carboxylate; 2,2,5,5-tetramethyl-3-pyrroline-1-oxy-3-carboxylic acid; 2,2,6,6-tetramethylpiperidine-1-oxy; 4-amino-2,2,6,6-tetramethylpiperadine-1-oxy; 4-carboxy-2,2,6,6-tetramethylpiperadine-1-oxy; 4-acetamido-2,2,6,6-tetramethylpiperadine-1-oxy; 4-bromo-2,2,6,6-tetramethylpiperadine-1-oxy; 4-(N,N-dimethyl-N-(2-hydroxyethyl))ammonium-2,2,6,6-tetramethylpiperidine-1-oxy; 4-(N,N-dimethyl-N-(3-sulfopropyl)ammonium-2,2,6,6-tetramethylpiperidine-1-oxy; N-(4-(iodoacetyl)amino-2,2,6,6 tetramethylpiperidine-1-oxy; N-(2,2,6,6-tetramethylpiperidine-1-oxy-4-yl)maleimide; and mixtures thereof.

6. The method of claim 5 where the drug or agent is a 2,2,6,6-tetramethylpiperadine-1-oxy.

7. The method of claim 4 where the drug or agent is gallium nitrate.

8. The method of claim 4 further comprising chemically conjugating a 2,2,6,6-tetramethylpiperadine-1-oxy compound to the polymer.

9. A fibrous membrane comprising biodegradable electrospun poly(ester-amide) for use for biomedical application, wherein:
the fibrous membrane has an average fiber diameter ranging from 300 nm-1.2 μm, a median pore size ranging from 0.1 to 100 micrometer, a surface area ranging from 10 to 300 $m^2$/g, and an average thickness ranging from 0.01 to 0.500 mm, and the fibrous membrane comprises a drug or agent, wherein the electrospun poly(ester-amide) is electrospun from a solution prepared from poly(ester-amide) dissolved in a mixture of chloroform and dimethylformamide (DMF).

10. The fibrous membrane of claim 9 wherein the ratio of chloroform to DMF in the mixture is 1.8-2.2 to 1.0.

11. The method of claim 4 wherein the ratio of chloroform to DMF in the mixture is 1.8-2.2 to 1.0.

* * * * *